US009309297B2

(12) United States Patent
Nandy et al.

(10) Patent No.: US 9,309,297 B2
(45) Date of Patent: Apr. 12, 2016

(54) DNA SEQUENCE, AND RECOMBINANT PREPARATION OF GROUP 4 MAJOR ALLERGENS FROM CEREALS

(75) Inventors: Andreas Nandy, Hamburg (DE); Helmut Fiebig, Schwarzenbek (DE); Oliver Cromwell, Suesel-Fassendorf (DE)

(73) Assignee: MERCK PATENT GMBH, Darmstadt (DE)

( * ) Notice: Subject to any disclaimer, the term of this patent is extended or adjusted under 35 U.S.C. 154(b) by 914 days.

(21) Appl. No.: 12/947,361

(22) Filed: Nov. 16, 2010

(65) Prior Publication Data

US 2013/0164313 A1  Jun. 27, 2013

Related U.S. Application Data

(62) Division of application No. 10/583,089, filed as application No. PCT/EP2004/013664 on Dec. 1, 2004, now Pat. No. 7,935,347.

(30) Foreign Application Priority Data

Dec. 16, 2003 (DE) .................................. 103 59 351

(51) Int. Cl.
| | |
|---|---|
| *A01N 63/00* | (2006.01) |
| *A61K 48/00* | (2006.01) |
| *C07H 21/02* | (2006.01) |
| *C07H 21/04* | (2006.01) |
| *C12N 1/12* | (2006.01) |
| *C12N 1/20* | (2006.01) |
| *C12N 15/00* | (2006.01) |
| *C12N 15/09* | (2006.01) |
| *C12P 21/04* | (2006.01) |
| *C12P 21/06* | (2006.01) |
| *C07K 14/415* | (2006.01) |
| *A61K 39/00* | (2006.01) |
| *A61K 38/00* | (2006.01) |

(52) U.S. Cl.
CPC ............... *C07K 14/415* (2013.01); *A61K 38/00* (2013.01); *A61K 2039/53* (2013.01)

(58) Field of Classification Search
None
See application file for complete search history.

(56) References Cited

U.S. PATENT DOCUMENTS

| | | | |
|---|---|---|---|
| 5,762,943 A | 6/1998 | Dolovich et al. | |
| 7,214,786 B2 * | 5/2007 | Kovalic et al. | 536/23.6 |
| 2005/0074464 A1 | 4/2005 | Deweerd | |
| 2006/0177470 A1 | 8/2006 | Fiebig et al. | |

FOREIGN PATENT DOCUMENTS

| | | |
|---|---|---|
| WO | WO 03025008 | 3/2003 |
| WO | WO 2004/000881 | 12/2003 |
| WO | WO 04000881 | 12/2003 |

OTHER PUBLICATIONS

Genbank Accession No. AP003544.1 published in 2001.*
Meinkoth et al. 'Hybridization of nucleic acids immobilized on solid supports.' Anal. Biochem. 138:267-284, 1984.*
Tarzi et al., "Peptide Immunotherapy for Allergic Disease", Expert Opinion Biol. Therap., 3 (4): 617-626, 2003.
Gavrovic et al., "Microheterogeneity Examination of Grass Group 4 Allergens", Allergy, 53 (Suppl. 43): 27, 1998.
Stumvoll S et al: "Purification, Structural and Immunological Chacateriaztion of a Timothy Grass (*Phleium pratense*) Pollen Allergen, Phl P 4, With Cross-Reactive Potential" Biological Chemistry, Bd. 383, Nor. 9, Sep. 2002, XP002260346.
Astwood J D et al: "Cloning and Expression Pattern of Hor V 9, The Group 9 Pollen Isoallergen From Barley" Gene: An International Journal of Genese and Genomes,Elsevier Science Publishers, Barking, GB, Bd. 182, Nr. 1-2 Dec. 5 1996, XP004071930.
Rihs H P et al: "Polymerase Chain Reaction Based CDNA Clonong of Wheat Profilin: A Potential Plant Allergen" International Archives of Allergy and Immunology, Bd. 105, Jan. 1994, XP000604627.
Fahlbusch B et al: Detection and Quantification of Group 4 Allergens in Grass Pollen Extracts Using Monoclonal Antibodies: Clinical and Experimental Allergy, Blackwell Scientific Publications, London, GB, Bd. 28, Nr. 7, Jul. 1998, XP002260345.
Database EMBL'Online! 19. Nov. 2004 XP002325590.
Database EMBL 19. Nov. 2004, XP002325591.
Database ENBL 19. Nov. 2004, XP002332685.
Database ENBL 19. Nov. 2004, XP002332686.
Database EMBL 19. Nov. 2004, XP002332687.
Martis et al. "The Genome Structure of Rye (*Secale cereal*L.) and Its Multiple Parents." W400. Plant & Animal Genome XXI; San Diego, CA. Jan. 14, 2013.
Li et al. "High levels of nucleotide diversity and fast decline of linkage disequilibrium in rye (*Secale cereale* L.) genes involved in frost response." BMC Plant Biology, 11:6, 2011.
Becker et al. "Dna sequence and recombinant production of the grass pollen allergen phl p4". Publication No. WO2004000881 A1—Publication Date: Dec. 31, 2003—(English Machine Translation).

* cited by examiner

*Primary Examiner* — Nora Rooney
(74) *Attorney, Agent, or Firm* — Millen, White, Zelano, Branigan, P.C.

(57) ABSTRACT

The present invention relates to the provision of DNA sequences of group 4 major allergens from cereals. The invention also encompasses fragments, new combinations of partial sequences and point mutants having a hypoallergenic action. The recombinant DNA molecules and the derived polypeptides, fragments, new combinations of partial sequences and variants can be utilized for the therapy of pollen-allergic diseases. The proteins prepared by recombinant methods can be employed for in vitro and in vivo diagnosis of pollen allergies.

11 Claims, No Drawings

SEQUENCE LISTING

<160> NUMBER OF SEQ ID NOS: 44

<210> SEQ ID NO 1
<211> LENGTH: 1603
<212> TYPE: DNA
<213> ORGANISM: Secale cereale

```
<220> FEATURE:
<221> NAME/KEY: CDS
<222> LOCATION: (1)..(1557)

<400> SEQUENCE: 1
```

| | | | | | | | | | | | | | | | | |
|---|---|---|---|---|---|---|---|---|---|---|---|---|---|---|---|---|
| aac | tat | agg | gcc | ttc | gcg | ctg | gcg | ctc | ctc | ttc | tgc | gcc | ttg | tcc | tgc | 48 |
| Asn | Tyr | Arg | Ala | Phe | Ala | Leu | Ala | Leu | Leu | Phe | Cys | Ala | Leu | Ser | Cys | |
| 1 | | | | 5 | | | | | 10 | | | | | 15 | | |
| caa | gcc | gcc | gcg | gcc | gcc | tac | gcg | ccc | gtg | cct | gcc | aag | gcg | gac | ttc | 96 |
| Gln | Ala | Ala | Ala | Ala | Ala | Tyr | Ala | Pro | Val | Pro | Ala | Lys | Ala | Asp | Phe | |
| | | 20 | | | | | 25 | | | | | 30 | | | | |
| ctc | gga | tgc | ctc | atg | aag | gag | ata | ccg | gcc | cgc | ctc | ctc | tac | gcc | aag | 144 |
| Leu | Gly | Cys | Leu | Met | Lys | Glu | Ile | Pro | Ala | Arg | Leu | Leu | Tyr | Ala | Lys | |
| | 35 | | | | | 40 | | | | | 45 | | | | | |
| agc | tcg | cct | gac | tac | ccc | acc | gtg | ctg | gcg | cag | acc | atc | agg | aac | tcg | 192 |
| Ser | Ser | Pro | Asp | Tyr | Pro | Thr | Val | Leu | Ala | Gln | Thr | Ile | Arg | Asn | Ser | |
| 50 | | | | | 55 | | | | | 60 | | | | | | |
| cgg | tgg | tcg | tcg | ccg | cag | aac | gtg | aag | ccg | atc | tac | atc | atc | acc | ccc | 240 |
| Arg | Trp | Ser | Ser | Pro | Gln | Asn | Val | Lys | Pro | Ile | Tyr | Ile | Ile | Thr | Pro | |
| 65 | | | | | 70 | | | | | 75 | | | | | 80 | |
| acc | aac | gcc | tcg | cac | atc | cag | tcc | gcg | gtg | gtg | tgc | ggc | cgc | cgg | cac | 288 |
| Thr | Asn | Ala | Ser | His | Ile | Gln | Ser | Ala | Val | Val | Cys | Gly | Arg | Arg | His | |
| | | | | 85 | | | | | 90 | | | | | 95 | | |
| ggc | atc | cgc | ctc | cgc | gtg | cgg | agc | ggc | ggc | cac | gac | tac | gag | ggc | ctg | 336 |
| Gly | Ile | Arg | Leu | Arg | Val | Arg | Ser | Gly | Gly | His | Asp | Tyr | Glu | Gly | Leu | |
| | | 100 | | | | | 105 | | | | | 110 | | | | |
| tcg | tac | cgg | tct | gag | aaa | ccc | gag | acg | ttc | gcc | gtc | gtc | gac | ctc | aac | 384 |
| Ser | Tyr | Arg | Ser | Glu | Lys | Pro | Glu | Thr | Phe | Ala | Val | Val | Asp | Leu | Asn | |
| | | | 115 | | | | | 120 | | | | | 125 | | | |
| aag | atg | cgg | gca | gtg | tcg | gtc | gac | ggc | tac | gcc | cgg | acg | gcg | tgg | gtc | 432 |
| Lys | Met | Arg | Ala | Val | Ser | Val | Asp | Gly | Tyr | Ala | Arg | Thr | Ala | Trp | Val | |
| | | | | 130 | | | | | 135 | | | | | 140 | | |
| gaa | tcc | ggc | gcg | cag | ctc | ggc | gag | ctc | tac | tac | gcg | atc | gcc | aag | aac | 480 |
| Glu | Ser | Gly | Ala | Gln | Leu | Gly | Glu | Leu | Tyr | Tyr | Ala | Ile | Ala | Lys | Asn | |
| 145 | | | | | 150 | | | | | 155 | | | | | 160 | |
| agc | ccc | gtg | ctc | gcg | ttc | ccg | gct | ggc | gtc | tgc | ccg | tcc | atc | ggc | gtc | 528 |
| Ser | Pro | Val | Leu | Ala | Phe | Pro | Ala | Gly | Val | Cys | Pro | Ser | Ile | Gly | Val | |
| | | | | 165 | | | | | 170 | | | | | 175 | | |
| ggc | ggc | aac | ttc | gca | ggc | ggc | ggc | ttt | ggc | atg | ctg | ctg | cgc | aag | tac | 576 |
| Gly | Gly | Asn | Phe | Ala | Gly | Gly | Gly | Phe | Gly | Met | Leu | Leu | Arg | Lys | Tyr | |
| | | | 180 | | | | | 185 | | | | | 190 | | | |
| ggc | atc | gcc | gct | gag | aac | gtc | atc | gac | gtc | aag | gtg | gtc | gac | ccc | aac | 624 |
| Gly | Ile | Ala | Ala | Glu | Asn | Val | Ile | Asp | Val | Lys | Val | Val | Asp | Pro | Asn | |
| | | | 195 | | | | | 200 | | | | | 205 | | | |
| ggc | aag | ctg | ctc | gac | aag | agc | tcc | atg | agc | gcg | gac | cac | ttc | tgg | gcc | 672 |
| Gly | Lys | Leu | Leu | Asp | Lys | Ser | Ser | Met | Ser | Ala | Asp | His | Phe | Trp | Ala | |
| | 210 | | | | | 215 | | | | | 220 | | | | | |
| gtt | agg | ggc | ggc | gga | gag | agc | ttt | ggc | atc | gtc | gtc | tcg | tgg | cag | | 720 |
| Val | Arg | Gly | Gly | Gly | Glu | Ser | Phe | Gly | Ile | Val | Val | Ser | Trp | Gln | | |
| 225 | | | | | 230 | | | | | 235 | | | | | 240 | |
| gtg | aag | ctc | ctg | ccg | gtg | cct | ccc | acc | gtg | acc | gtc | ctc | aag | atc | ccc | 768 |
| Val | Lys | Leu | Leu | Pro | Val | Pro | Pro | Thr | Val | Thr | Val | Leu | Lys | Ile | Pro | |
| | | | | 245 | | | | | 250 | | | | | 255 | | |
| aag | acg | gtg | caa | gaa | ggc | gcc | ata | gac | ctc | gtc | aac | aag | tgg | cag | ctg | 816 |
| Lys | Thr | Val | Gln | Glu | Gly | Ala | Ile | Asp | Leu | Val | Asn | Lys | Trp | Gln | Leu | |
| | | | 260 | | | | | 265 | | | | | 270 | | | |
| gtc | ggg | ccg | gca | ctt | ccc | ggc | gac | ctc | atg | atc | cgc | atc | atc | ctt | gcc | 864 |
| Val | Gly | Pro | Ala | Leu | Pro | Gly | Asp | Leu | Met | Ile | Arg | Ile | Ile | Leu | Ala | |
| | | | 275 | | | | | 280 | | | | | 285 | | | |
| ggg | aac | agc | gcg | acg | ttc | gag | gcc | atg | tac | ctg | ggc | acc | tgc | agt | acc | 912 |

-continued

```
                Gly Asn Ser Ala Thr Phe Glu Ala Met Tyr Leu Gly Thr Cys Ser Thr
                        290                 295                 300 ctg acg ccg ctg atg agc agc aaa ttc ccc gag ctt ggc atg aac ccc        960
Leu Thr Pro Leu Met Ser Ser Lys Phe Pro Glu Leu Gly Met Asn Pro
305                 310                 315                 320 tcg cac tgc aac gag atg tcc tgg atc aag tcc atc ccc ttc atc cac       1008
Ser His Cys Asn Glu Met Ser Trp Ile Lys Ser Ile Pro Phe Ile His
                325                 330                 335 ctc ggc aag cag aac ctc gac gac ctc ctc aac cgg aac aac acc ttc       1056
Leu Gly Lys Gln Asn Leu Asp Asp Leu Leu Asn Arg Asn Asn Thr Phe
            340                 345                 350 aaa cca ttc gcc gaa tac aag tcg gac tac gtg tac cag ccc ttc ccc       1104
Lys Pro Phe Ala Glu Tyr Lys Ser Asp Tyr Val Tyr Gln Pro Phe Pro
        355                 360                 365 aag ccc gtg tgg gag cag atc ttc ggc tgg ctt gtg aag ccc ggc gcg       1152
Lys Pro Val Trp Glu Gln Ile Phe Gly Trp Leu Val Lys Pro Gly Ala
    370                 375                 380 ggg atc atg atc atg gac ccc tat ggc gcc acc atc agc gct acc ccc       1200
Gly Ile Met Ile Met Asp Pro Tyr Gly Ala Thr Ile Ser Ala Thr Pro
385                 390                 395                 400 gaa gcg gcg acg ccg ttc cct cac cgc cag ggc gtc ctc ttc aac atc       1248
Glu Ala Ala Thr Pro Phe Pro His Arg Gln Gly Val Leu Phe Asn Ile
                405                 410                 415 cag tac gtc aac tac tgg ttc gct gag tca gcc ggc gcg gcg ccg ctg       1296
Gln Tyr Val Asn Tyr Trp Phe Ala Glu Ser Ala Gly Ala Ala Pro Leu
            420                 425                 430 cag tgg agc aag gac ata tac aag ttc atg gag ccg tac gtg agc aaa       1344
Gln Trp Ser Lys Asp Ile Tyr Lys Phe Met Glu Pro Tyr Val Ser Lys
        435                 440                 445 aat ccc agg cag gcg tat gcc aac tac agg gac atc gac ctt ggc agg       1392
Asn Pro Arg Gln Ala Tyr Ala Asn Tyr Arg Asp Ile Asp Leu Gly Arg
    450                 455                 460 aat gag gtg gtg aac gac atc tcc acc tac agc agc ggc aaa gtg tgg       1440
Asn Glu Val Val Asn Asp Ile Ser Thr Tyr Ser Ser Gly Lys Val Trp
465                 470                 475                 480 ggt gag aag tac ttc aag ggc aac ttc caa agg ctc gcc att acc aag       1488
Gly Glu Lys Tyr Phe Lys Gly Asn Phe Gln Arg Leu Ala Ile Thr Lys
                485                 490                 495 ggc aag gtg gat cct cag gac tac ttc agg aac gag cag agc atc ccg       1536
Gly Lys Val Asp Pro Gln Asp Tyr Phe Arg Asn Glu Gln Ser Ile Pro
            500                 505                 510 cca ctg gtc gag aag tac tga tcgaggacct tgcatggaaa tttagtgcgt          1587
Pro Leu Val Glu Lys Tyr
        515 ggttggcgtt tcacat                                                     1603
```

<210> SEQ ID NO 2
<211> LENGTH: 518
<212> TYPE: PRT
<213> ORGANISM: Secale cereale

<400> SEQUENCE: 2

```
Asn Tyr Arg Ala Phe Ala Leu Ala Leu Leu Phe Cys Ala Leu Ser Cys
 1               5                  10                  15

Gln Ala Ala Ala Ala Tyr Ala Pro Val Pro Ala Lys Ala Asp Phe
             20                  25                  30

Leu Gly Cys Leu Met Lys Glu Ile Pro Ala Arg Leu Leu Tyr Ala Lys
         35                  40                  45

Ser Ser Pro Asp Tyr Pro Thr Val Leu Ala Gln Thr Ile Arg Asn Ser
```

-continued

```
                50                  55                  60
Arg Trp Ser Ser Pro Gln Asn Val Lys Pro Ile Tyr Ile Ile Thr Pro
 65                      70                  75                  80

Thr Asn Ala Ser His Ile Gln Ser Ala Val Val Cys Gly Arg Arg His
                     85                  90                  95

Gly Ile Arg Leu Arg Val Arg Ser Gly Gly His Asp Tyr Glu Gly Leu
                100                 105                 110

Ser Tyr Arg Ser Glu Lys Pro Glu Thr Phe Ala Val Val Asp Leu Asn
                115                 120                 125

Lys Met Arg Ala Val Ser Val Asp Gly Tyr Ala Arg Thr Ala Trp Val
                130                 135                 140

Glu Ser Gly Ala Gln Leu Gly Glu Leu Tyr Tyr Ala Ile Ala Lys Asn
145                 150                 155                 160

Ser Pro Val Leu Ala Phe Pro Ala Gly Val Cys Pro Ser Ile Gly Val
                165                 170                 175

Gly Gly Asn Phe Ala Gly Gly Phe Gly Met Leu Leu Arg Lys Tyr
                180                 185                 190

Gly Ile Ala Ala Glu Asn Val Ile Asp Val Lys Val Asp Pro Asn
                195                 200                 205

Gly Lys Leu Leu Asp Lys Ser Ser Met Ser Ala Asp His Phe Trp Ala
                210                 215                 220

Val Arg Gly Gly Gly Glu Ser Phe Gly Ile Val Val Ser Trp Gln
225                 230                 235                 240

Val Lys Leu Leu Pro Val Pro Thr Val Thr Val Leu Lys Ile Pro
                245                 250                 255

Lys Thr Val Gln Glu Gly Ala Ile Asp Leu Val Asn Lys Trp Gln Leu
                260                 265                 270

Val Gly Pro Ala Leu Pro Gly Asp Leu Met Ile Arg Ile Ile Leu Ala
                275                 280                 285

Gly Asn Ser Ala Thr Phe Glu Ala Met Tyr Leu Gly Thr Cys Ser Thr
                290                 295                 300

Leu Thr Pro Leu Met Ser Ser Lys Phe Pro Glu Leu Gly Met Asn Pro
305                 310                 315                 320

Ser His Cys Asn Glu Met Ser Trp Ile Lys Ser Ile Pro Phe Ile His
                325                 330                 335

Leu Gly Lys Gln Asn Leu Asp Asp Leu Leu Asn Arg Asn Asn Thr Phe
                340                 345                 350

Lys Pro Phe Ala Glu Tyr Lys Ser Asp Tyr Val Tyr Gln Pro Phe Pro
                355                 360                 365

Lys Pro Val Trp Glu Gln Ile Phe Gly Trp Leu Val Lys Pro Gly Ala
                370                 375                 380

Gly Ile Met Ile Met Asp Pro Tyr Gly Ala Thr Ile Ser Ala Thr Pro
385                 390                 395                 400

Glu Ala Ala Thr Pro Phe Pro His Arg Gln Gly Val Leu Phe Asn Ile
                405                 410                 415

Gln Tyr Val Asn Tyr Trp Phe Ala Glu Ser Ala Gly Ala Ala Pro Leu
                420                 425                 430

Gln Trp Ser Lys Asp Ile Tyr Lys Phe Met Glu Pro Tyr Val Ser Lys
                435                 440                 445

Asn Pro Arg Gln Ala Tyr Ala Asn Tyr Arg Asp Ile Asp Leu Gly Arg
                450                 455                 460

Asn Glu Val Val Asn Asp Ile Ser Thr Tyr Ser Ser Gly Lys Val Trp
465                 470                 475                 480
```

```
Gly Glu Lys Tyr Phe Lys Gly Asn Phe Gln Arg Leu Ala Ile Thr Lys
                485                 490                 495

Gly Lys Val Asp Pro Gln Asp Tyr Phe Arg Asn Glu Gln Ser Ile Pro
            500                 505                 510

Pro Leu Val Glu Lys Tyr
            515

<210> SEQ ID NO 3
<211> LENGTH: 1644
<212> TYPE: DNA
<213> ORGANISM: Secale cereale
<220> FEATURE:
<221> NAME/KEY: CDS
<222> LOCATION: (1)..(1563)

<400> SEQUENCE: 3 aac tcg agg gcc ttt gct ctg gtg ccc ctc ctc atc tgc gtc ttg tcc      48
Asn Ser Arg Ala Phe Ala Leu Val Pro Leu Leu Ile Cys Val Leu Ser
  1               5                  10                  15 tgc cac gcc gcc gtc tcc tac gcg gcg gcg ccg gtg ccg gcc aag gag      96
Cys His Ala Ala Val Ser Tyr Ala Ala Ala Pro Val Pro Ala Lys Glu
             20                  25                  30 gac ttc ttc gga tgc ctg gtg aag gag ata ccg gcc cgc ctc ctc tac     144
Asp Phe Phe Gly Cys Leu Val Lys Glu Ile Pro Ala Arg Leu Leu Tyr
         35                  40                  45 gcc aag agc tcg cct gcc ttc ccc acc gtc ctg gcg cag acc atc agg     192
Ala Lys Ser Ser Pro Ala Phe Pro Thr Val Leu Ala Gln Thr Ile Arg
     50                  55                  60 aac tcg cgg tgg tcg tcg ccg cag agc gtg aag ccg ctc tac atc atc     240
Asn Ser Arg Trp Ser Ser Pro Gln Ser Val Lys Pro Leu Tyr Ile Ile
 65                  70                  75                  80 acc ccc acc aac gcc tcc cac atc cag tcc gcg gtg gtg tgc ggc cgc     288
Thr Pro Thr Asn Ala Ser His Ile Gln Ser Ala Val Val Cys Gly Arg
                 85                  90                  95 cgg cac ggc gtc cgc atc cgc gtg cgg agc ggc ggc cac gac tac gag     336
Arg His Gly Val Arg Ile Arg Val Arg Ser Gly Gly His Asp Tyr Glu
            100                 105                 110 ggc ctg tcg tac cgg tcc gag cgc ccc gag gcg ttc gcc gtc gtc gac     384
Gly Leu Ser Tyr Arg Ser Glu Arg Pro Glu Ala Phe Ala Val Val Asp
        115                 120                 125 ctc aac aag atg cgg gcc gtg gtg gtc gac ggc aag gct cgc acg gcg     432
Leu Asn Lys Met Arg Ala Val Val Val Asp Gly Lys Ala Arg Thr Ala
    130                 135                 140 tgg gtg gac tcc ggt gcg cag ctc ggc gag ctc tac tac gcc atc gcc     480
Trp Val Asp Ser Gly Ala Gln Leu Gly Glu Leu Tyr Tyr Ala Ile Ala
145                 150                 155                 160 aag aac agc ccc gtg ctc gcg ttc ccg gcc ggc gtt tgc ccg acc att     528
Lys Asn Ser Pro Val Leu Ala Phe Pro Ala Gly Val Cys Pro Thr Ile
                165                 170                 175 ggt gta ggc ggc aac ttc gct ggc ggc ggc ttc ggc atg ctg ctg cgc     576
Gly Val Gly Gly Asn Phe Ala Gly Gly Gly Phe Gly Met Leu Leu Arg
            180                 185                 190 aag tac ggc atc gcc gcc gag aac gtc atc gac gtg aag gtg gtc gac     624
Lys Tyr Gly Ile Ala Ala Glu Asn Val Ile Asp Val Lys Val Val Asp
        195                 200                 205 gcc aac ggc aca ctg ctc gac aag agc tcc atg agc gcg gat cac ttc     672
Ala Asn Gly Thr Leu Leu Asp Lys Ser Ser Met Ser Ala Asp His Phe
    210                 215                 220 tgg gcc gtc agg ggc ggc ggc gga gag agc ttc ggc atc gtc gtg tcg     720
Trp Ala Val Arg Gly Gly Gly Gly Glu Ser Phe Gly Ile Val Val Ser
225                 230                 235                 240
```

```
           225                 230                 235                 240
tgg cag gtg aag ctc ctc ccg gtg cct ccc acc gtg acc gtc ttc aag         768
Trp Gln Val Lys Leu Leu Pro Val Pro Pro Thr Val Thr Val Phe Lys
                245                 250                 255 atc ccc aag acg gtg caa gaa ggc gcc gta gag ctc atc aac aag tgg         816
Ile Pro Lys Thr Val Gln Glu Gly Ala Val Glu Leu Ile Asn Lys Trp
                260                 265                 270 cag cta gtc gcg ccg gcc ctc ccc gac gac ctg atg atc cgc atc atc         864
Gln Leu Val Ala Pro Ala Leu Pro Asp Asp Leu Met Ile Arg Ile Ile
                275                 280                 285 gct ttc ggc ggc acc gcc aag ttc gag gcc atg tac ctg ggc acc tgc         912
Ala Phe Gly Gly Thr Ala Lys Phe Glu Ala Met Tyr Leu Gly Thr Cys
            290                 295                 300 aaa gcc ctg aca ccg ctg atg agc agc aga ttc ccc gag ctc ggc atg         960
Lys Ala Leu Thr Pro Leu Met Ser Ser Arg Phe Pro Glu Leu Gly Met
305                 310                 315                 320 aac gcc tcg cac tgc aac gag atg ccc tgg atc aag tcc gtc cca ttc        1008
Asn Ala Ser His Cys Asn Glu Met Pro Trp Ile Lys Ser Val Pro Phe
                325                 330                 335 atc cac ctt ggc aag cag gcc acc ctc tcc gac ctc ctc aac cgg aac        1056
Ile His Leu Gly Lys Gln Ala Thr Leu Ser Asp Leu Leu Asn Arg Asn
                340                 345                 350 aac acc ttc aaa ccc ttc gcc gag tac aag tcg gac tac gtc tac cag        1104
Asn Thr Phe Lys Pro Phe Ala Glu Tyr Lys Ser Asp Tyr Val Tyr Gln
                355                 360                 365 ccc gtc ccc aag ccc gtc tgg gcg cag atc ttc gtc tgg ctc gtc aaa        1152
Pro Val Pro Lys Pro Val Trp Ala Gln Ile Phe Val Trp Leu Val Lys
            370                 375                 380 ccc ggc gcc ggg atc atg gtc atg gac ccc tac ggc gcc gcc atc agc        1200
Pro Gly Ala Gly Ile Met Val Met Asp Pro Tyr Gly Ala Ala Ile Ser
385                 390                 395                 400 gcc acc ccc gaa gcc gcc acg ccg ttc cct cac cgc aag gac gtc ctc        1248
Ala Thr Pro Glu Ala Ala Thr Pro Phe Pro His Arg Lys Asp Val Leu
                405                 410                 415 ttc aac atc cag tac gtc aac tac tgg ttc gac gag gca ggc ggc gcc        1296
Phe Asn Ile Gln Tyr Val Asn Tyr Trp Phe Asp Glu Ala Gly Gly Ala
                420                 425                 430 gcg ccg ctg cag tgg agc aag gac atg tac agg ttc atg gag ccg tac        1344
Ala Pro Leu Gln Trp Ser Lys Asp Met Tyr Arg Phe Met Glu Pro Tyr
            435                 440                 445 gtc agc aag aac ccc aga cag gcc tac gcc aac tac agg gac atc gac        1392
Val Ser Lys Asn Pro Arg Gln Ala Tyr Ala Asn Tyr Arg Asp Ile Asp
450                 455                 460 ctc ggc agg aac gag gtg gtc aac gac atc tcc acc tat gcc agc ggc        1440
Leu Gly Arg Asn Glu Val Val Asn Asp Ile Ser Thr Tyr Ala Ser Gly
465                 470                 475                 480 aag gtc tgg ggc gag aag tac ttc aag ggc aac ttc caa agg ctc gcc        1488
Lys Val Trp Gly Glu Lys Tyr Phe Lys Gly Asn Phe Gln Arg Leu Ala
                485                 490                 495 att acc aag ggc aag gtg gat cct cag gac tac ttc agg aac gag cag        1536
Ile Thr Lys Gly Lys Val Asp Pro Gln Asp Tyr Phe Arg Asn Glu Gln
                500                 505                 510 agc atc ccg ccg ctg cta ggg aag tag tagtactctt gcttgcatgg              1583
Ser Ile Pro Pro Leu Leu Gly Lys
                515                 520 agatttgtag tgcgtctttc gcgtttcaaa tgcccaacta gtagaataag gatcgtgcgt      1643
a                                                                     1644
```

```
<210> SEQ ID NO 4
<211> LENGTH: 520
<212> TYPE: PRT
<213> ORGANISM: Secale cereale

<400> SEQUENCE: 4
```

| | | | | | | | | | | | | | | |
|---|---|---|---|---|---|---|---|---|---|---|---|---|---|---|
| Asn | Ser | Arg | Ala | Phe | Ala | Leu | Val | Pro | Leu | Leu | Ile | Cys | Val | Leu | Ser |
| 1 | | | | 5 | | | | | 10 | | | | | 15 | |
| Cys | His | Ala | Ala | Val | Ser | Tyr | Ala | Ala | Ala | Pro | Val | Pro | Ala | Lys | Glu |
| | | | 20 | | | | | 25 | | | | | 30 | | |
| Asp | Phe | Phe | Gly | Cys | Leu | Val | Lys | Glu | Ile | Pro | Ala | Arg | Leu | Leu | Tyr |
| | | 35 | | | | | 40 | | | | | 45 | | | |
| Ala | Lys | Ser | Ser | Pro | Ala | Phe | Pro | Thr | Val | Leu | Ala | Gln | Thr | Ile | Arg |
| 50 | | | | | 55 | | | | | 60 | | | | | |
| Asn | Ser | Arg | Trp | Ser | Ser | Pro | Gln | Ser | Val | Lys | Pro | Leu | Tyr | Ile | Ile |
| 65 | | | | 70 | | | | | 75 | | | | | 80 | |
| Thr | Pro | Thr | Asn | Ala | Ser | His | Ile | Gln | Ser | Ala | Val | Val | Cys | Gly | Arg |
| | | | | 85 | | | | | 90 | | | | | 95 | |
| Arg | His | Gly | Val | Arg | Ile | Arg | Val | Arg | Ser | Gly | Gly | His | Asp | Tyr | Glu |
| | | | 100 | | | | | 105 | | | | | 110 | | |
| Gly | Leu | Ser | Tyr | Arg | Ser | Glu | Arg | Pro | Glu | Ala | Phe | Ala | Val | Val | Asp |
| | | 115 | | | | | 120 | | | | | 125 | | | |
| Leu | Asn | Lys | Met | Arg | Ala | Val | Val | Asp | Gly | Lys | Ala | Arg | Thr | Ala |
| 130 | | | | | 135 | | | | | 140 | | | | | |
| Trp | Val | Asp | Ser | Gly | Ala | Gln | Leu | Gly | Glu | Leu | Tyr | Tyr | Ala | Ile | Ala |
| 145 | | | | | 150 | | | | | 155 | | | | | 160 |
| Lys | Asn | Ser | Pro | Val | Leu | Ala | Phe | Pro | Ala | Gly | Val | Cys | Pro | Thr | Ile |
| | | | | 165 | | | | | 170 | | | | | 175 | |
| Gly | Val | Gly | Gly | Asn | Phe | Ala | Gly | Gly | Gly | Phe | Gly | Met | Leu | Leu | Arg |
| | | | 180 | | | | | 185 | | | | | 190 | | |
| Lys | Tyr | Gly | Ile | Ala | Ala | Glu | Asn | Val | Ile | Asp | Val | Lys | Val | Val | Asp |
| | | 195 | | | | | 200 | | | | | 205 | | | |
| Ala | Asn | Gly | Thr | Leu | Leu | Asp | Lys | Ser | Ser | Met | Ser | Ala | Asp | His | Phe |
| 210 | | | | | 215 | | | | | 220 | | | | | |
| Trp | Ala | Val | Arg | Gly | Gly | Gly | Glu | Ser | Phe | Gly | Ile | Val | Val | Ser |
| 225 | | | | | 230 | | | | | 235 | | | | | 240 |
| Trp | Gln | Val | Lys | Leu | Leu | Pro | Val | Pro | Thr | Val | Thr | Val | Phe | Lys |
| | | | | 245 | | | | | 250 | | | | | 255 | |
| Ile | Pro | Lys | Thr | Val | Gln | Glu | Gly | Ala | Val | Glu | Leu | Ile | Asn | Lys | Trp |
| | | | 260 | | | | | 265 | | | | | 270 | | |
| Gln | Leu | Val | Ala | Pro | Ala | Leu | Pro | Asp | Asp | Leu | Met | Ile | Arg | Ile | Ile |
| | | 275 | | | | | 280 | | | | | 285 | | | |
| Ala | Phe | Gly | Gly | Thr | Ala | Lys | Phe | Glu | Ala | Met | Tyr | Leu | Gly | Thr | Cys |
| 290 | | | | | 295 | | | | | 300 | | | | | |
| Lys | Ala | Leu | Thr | Pro | Leu | Met | Ser | Ser | Arg | Phe | Pro | Glu | Leu | Gly | Met |
| 305 | | | | | 310 | | | | | 315 | | | | | 320 |
| Asn | Ala | Ser | His | Cys | Asn | Glu | Met | Pro | Trp | Ile | Lys | Ser | Val | Pro | Phe |
| | | | | 325 | | | | | 330 | | | | | 335 | |
| Ile | His | Leu | Gly | Lys | Gln | Ala | Thr | Leu | Ser | Asp | Leu | Leu | Asn | Arg | Asn |
| | | | 340 | | | | | 345 | | | | | 350 | | |
| Asn | Thr | Phe | Lys | Pro | Phe | Ala | Glu | Tyr | Lys | Ser | Asp | Tyr | Val | Tyr | Gln |
| | | 355 | | | | | 360 | | | | | 365 | | | |
| Pro | Val | Pro | Lys | Pro | Val | Trp | Ala | Gln | Ile | Phe | Val | Trp | Leu | Val | Lys |
| 370 | | | | | 375 | | | | | 380 | | | | | |

-continued

```
Pro Gly Ala Gly Ile Met Val Met Asp Pro Tyr Gly Ala Ala Ile Ser
385                 390                 395                 400

Ala Thr Pro Glu Ala Ala Thr Pro Phe Pro His Arg Lys Asp Val Leu
            405                 410                 415

Phe Asn Ile Gln Tyr Val Asn Tyr Trp Phe Asp Glu Ala Gly Gly Ala
        420                 425                 430

Ala Pro Leu Gln Trp Ser Lys Asp Met Tyr Arg Phe Met Glu Pro Tyr
            435                 440                 445

Val Ser Lys Asn Pro Arg Gln Ala Tyr Ala Asn Tyr Arg Asp Ile Asp
    450                 455                 460

Leu Gly Arg Asn Glu Val Val Asn Asp Ile Ser Thr Tyr Ala Ser Gly
465                 470                 475                 480

Lys Val Trp Gly Glu Lys Tyr Phe Lys Gly Asn Phe Gln Arg Leu Ala
                485                 490                 495

Ile Thr Lys Gly Lys Val Asp Pro Gln Asp Tyr Phe Arg Asn Glu Gln
            500                 505                 510

Ser Ile Pro Pro Leu Leu Gly Lys
            515                 520

<210> SEQ ID NO 5
<211> LENGTH: 1608
<212> TYPE: DNA
<213> ORGANISM: Hordeum vulgare
<220> FEATURE:
<221> NAME/KEY: CDS
<222> LOCATION: (1)..(1557)

<400> SEQUENCE: 5 agc tcg agg gcc ttc gct ctg gtg ctc ctc ctc tgc gcc ttg tcc tgc       48
Ser Ser Arg Ala Phe Ala Leu Val Leu Leu Leu Cys Ala Leu Ser Cys
  1               5                  10                  15 cac cac gct gcc gtc tcc tcc gcg cag gtg ccg gcc aag gac gac ttc       96
His His Ala Ala Val Ser Ser Ala Gln Val Pro Ala Lys Asp Asp Phe
             20                  25                  30 ctg gga tgc ctc gtg aag gag ata ccg gcc cgc ctc ctc ttc gcc aag      144
Leu Gly Cys Leu Val Lys Glu Ile Pro Ala Arg Leu Leu Phe Ala Lys
         35                  40                  45 agc tcg cct gcc ttc ccc gcc gtc ctg gag cag acc atc agg aac tcg      192
Ser Ser Pro Ala Phe Pro Ala Val Leu Glu Gln Thr Ile Arg Asn Ser
     50                  55                  60 cgg tgg tcg tcg ccg cag aac gtg aag ccg ctc tac atc atc acc ccc      240
Arg Trp Ser Ser Pro Gln Asn Val Lys Pro Leu Tyr Ile Ile Thr Pro
 65                  70                  75                  80 acc aac acc tcc cac atc cag tct gct gtg gtg tgc ggc cgc cgg cac      288
Thr Asn Thr Ser His Ile Gln Ser Ala Val Val Cys Gly Arg Arg His
                 85                  90                  95 ggc gtc cgc ctc cgc gtg cgg agc ggc ggc cac gac tac gag ggc ctg      336
Gly Val Arg Leu Arg Val Arg Ser Gly Gly His Asp Tyr Glu Gly Leu
            100                 105                 110 tcg tac cgg tcc gag cgc ccc gag gcg ttc gcc gtc gta gac ctc aac      384
Ser Tyr Arg Ser Glu Arg Pro Glu Ala Phe Ala Val Val Asp Leu Asn
        115                 120                 125 aag atg cgg acc gtg ttg gtc aac gaa aag gcc cgc acg gcg tgg gtg      432
Lys Met Arg Thr Val Leu Val Asn Glu Lys Ala Arg Thr Ala Trp Val
    130                 135                 140 gac tcc ggc gcg cag ctc ggc gag ctc tac tac gcc atc gcc aag aac      480
Asp Ser Gly Ala Gln Leu Gly Glu Leu Tyr Tyr Ala Ile Ala Lys Asn
145                 150                 155                 160 agc ccc gtg ctc gcg ttc cca gcc ggc gtt tgc ccg tcc att ggt gta      528
```

-continued

```
            Ser Pro Val Leu Ala Phe Pro Ala Gly Val Cys Pro Ser Ile Gly Val
                            165                 170                 175 ggt ggc aac ttc gct ggc ggc ggc ttc ggc atg ctg ctg cgc aag tac        576
Gly Gly Asn Phe Ala Gly Gly Gly Phe Gly Met Leu Leu Arg Lys Tyr
                180                 185                 190 ggc atc gcc gcc gag aac gtc atc gac gtc aag ctg gtc gac gcc aac        624
Gly Ile Ala Ala Glu Asn Val Ile Asp Val Lys Leu Val Asp Ala Asn
                195                 200                 205 ggc aag ctg ctc gac aag agc tcc atg agc ccg gac cac ttc tgg gcc        672
Gly Lys Leu Leu Asp Lys Ser Ser Met Ser Pro Asp His Phe Trp Ala
        210                 215                 220 gtc agg ggc ggc ggc gga gag agc ttc ggc atc gtc gtc tcg tgg cag        720
Val Arg Gly Gly Gly Gly Glu Ser Phe Gly Ile Val Val Ser Trp Gln
225                 230                 235                 240 gtg aag ctt ctc ccg gtg cct ccc acc gtg act gtg ttt cag atc ccc        768
Val Lys Leu Leu Pro Val Pro Pro Thr Val Thr Val Phe Gln Ile Pro
                245                 250                 255 aag aca gtg caa gaa ggc gcc gta gac ctc atc aac aag tgg cag ctg        816
Lys Thr Val Gln Glu Gly Ala Val Asp Leu Ile Asn Lys Trp Gln Leu
                260                 265                 270 gtc gcg ccg gcc ctt ccc ggc gac atc atg atc cgc atc atc gcc atg        864
Val Ala Pro Ala Leu Pro Gly Asp Ile Met Ile Arg Ile Ile Ala Met
            275                 280                 285 ggg gac aaa gcg acg ttc gag gcc atg tac ctg ggc acc tgc aaa acc        912
Gly Asp Lys Ala Thr Phe Glu Ala Met Tyr Leu Gly Thr Cys Lys Thr
        290                 295                 300 ctg acg ccg ctg atg agc agc aaa ttc ccg gag ctt ggc atg aac ccc        960
Leu Thr Pro Leu Met Ser Ser Lys Phe Pro Glu Leu Gly Met Asn Pro
305                 310                 315                 320 tcg cac tgc aac gag atg ccc tgg atc aag tcc atc ccc ttc atc cac       1008
Ser His Cys Asn Glu Met Pro Trp Ile Lys Ser Ile Pro Phe Ile His
                325                 330                 335 ctt ggc aag cag gcc acc ctg gcc gac ctc ctc aac cgg aac aac acc       1056
Leu Gly Lys Gln Ala Thr Leu Ala Asp Leu Leu Asn Arg Asn Asn Thr
                340                 345                 350 ttc aaa ccc ttc gcc gaa tac aag tcg gac tac gtc tac cag ccc gtc       1104
Phe Lys Pro Phe Ala Glu Tyr Lys Ser Asp Tyr Val Tyr Gln Pro Val
            355                 360                 365 ccc aag ccc gtg tgg gag cag ctc ttc ggc tgg ctc acg aaa ccc ggc       1152
Pro Lys Pro Val Trp Glu Gln Leu Phe Gly Trp Leu Thr Lys Pro Gly
        370                 375                 380 gcg ggg atc atg gtc atg gac cca tac ggc gcc acc atc agc gcc acc       1200
Ala Gly Ile Met Val Met Asp Pro Tyr Gly Ala Thr Ile Ser Ala Thr
385                 390                 395                 400 ccc gaa gcg gcg acg ccg ttc cct cac cgc aag ggc gtc ctc ttc aac       1248
Pro Glu Ala Ala Thr Pro Phe Pro His Arg Lys Gly Val Leu Phe Asn
                405                 410                 415 atc cag tac gtc aac tac tgg ttc gcc gag gca gcc ggc gcc gcg ccg       1296
Ile Gln Tyr Val Asn Tyr Trp Phe Ala Glu Ala Ala Gly Ala Ala Pro
                420                 425                 430 ctg cag tgg agc aag gac att tac aaa ttc atg gag ccg ttc gtg agc       1344
Leu Gln Trp Ser Lys Asp Ile Tyr Lys Phe Met Glu Pro Phe Val Ser
            435                 440                 445 aag aac ccc agg cag gcg tac gcc aac tac agg gac atc gac ctc ggc       1392
Lys Asn Pro Arg Gln Ala Tyr Ala Asn Tyr Arg Asp Ile Asp Leu Gly
        450                 455                 460 agg aac gag gtg gtg aac gac atc tca acc tac agc agc ggc aag gtg       1440
Arg Asn Glu Val Val Asn Asp Ile Ser Thr Tyr Ser Ser Gly Lys Val
465                 470                 475                 480
```

```
tgg ggc gag aag tac ttc aag ggc aac ttc caa agg ctc gcc atc acc         1488
Trp Gly Glu Lys Tyr Phe Lys Gly Asn Phe Gln Arg Leu Ala Ile Thr
            485                 490                 495 aag ggc aag gtg gat ccc cag gac tac ttc agg aac gag cag agc atc         1536
Lys Gly Lys Val Asp Pro Gln Asp Tyr Phe Arg Asn Glu Gln Ser Ile
            500                 505                 510 ccg ccg ctg ctg ggc aag tag tgaccgagag tcttgcatgg agatttgtag            1587
Pro Pro Leu Leu Gly Lys
            515 tgcgtgcttg gcgtttctga t                                                 1608
```

<210> SEQ ID NO 6
<211> LENGTH: 518
<212> TYPE: PRT
<213> ORGANISM: Hordeum vulgare

<400> SEQUENCE: 6

```
Ser Ser Arg Ala Phe Ala Leu Val Leu Leu Cys Ala Leu Ser Cys
 1               5                  10                  15

His His Ala Ala Val Ser Ser Ala Gln Val Pro Ala Lys Asp Asp Phe
                20                  25                  30

Leu Gly Cys Leu Val Lys Glu Ile Pro Ala Arg Leu Leu Phe Ala Lys
            35                  40                  45

Ser Ser Pro Ala Phe Pro Ala Val Leu Glu Gln Thr Ile Arg Asn Ser
        50                  55                  60

Arg Trp Ser Ser Pro Gln Asn Val Lys Pro Leu Tyr Ile Ile Thr Pro
 65                 70                  75                  80

Thr Asn Thr Ser His Ile Gln Ser Ala Val Val Cys Gly Arg Arg His
                85                  90                  95

Gly Val Arg Leu Arg Val Arg Ser Gly Gly His Asp Tyr Glu Gly Leu
            100                 105                 110

Ser Tyr Arg Ser Glu Arg Pro Glu Ala Phe Ala Val Val Asp Leu Asn
        115                 120                 125

Lys Met Arg Thr Val Leu Val Asn Glu Lys Ala Arg Thr Ala Trp Val
130                 135                 140

Asp Ser Gly Ala Gln Leu Gly Glu Leu Tyr Tyr Ala Ile Ala Lys Asn
145                 150                 155                 160

Ser Pro Val Leu Ala Phe Pro Ala Gly Val Cys Pro Ser Ile Gly Val
                165                 170                 175

Gly Gly Asn Phe Ala Gly Gly Phe Gly Met Leu Leu Arg Lys Tyr
            180                 185                 190

Gly Ile Ala Ala Glu Asn Val Ile Asp Val Lys Leu Val Asp Ala Asn
        195                 200                 205

Gly Lys Leu Leu Asp Lys Ser Ser Met Ser Pro Asp His Phe Trp Ala
210                 215                 220

Val Arg Gly Gly Gly Glu Ser Phe Gly Ile Val Val Ser Trp Gln
225                 230                 235                 240

Val Lys Leu Leu Pro Val Pro Thr Val Thr Val Phe Gln Ile Pro
                245                 250                 255

Lys Thr Val Gln Glu Gly Ala Val Asp Leu Ile Asn Lys Trp Gln Leu
            260                 265                 270

Val Ala Pro Ala Leu Pro Gly Asp Ile Met Ile Arg Ile Ile Ala Met
        275                 280                 285

Gly Asp Lys Ala Thr Phe Glu Ala Met Tyr Leu Gly Thr Cys Lys Thr
290                 295                 300
```

-continued

```
Leu Thr Pro Leu Met Ser Ser Lys Phe Pro Glu Leu Gly Met Asn Pro
305                 310                 315                 320

Ser His Cys Asn Glu Met Pro Trp Ile Lys Ser Ile Pro Phe Ile His
            325                 330                 335

Leu Gly Lys Gln Ala Thr Leu Ala Asp Leu Leu Asn Arg Asn Asn Thr
        340                 345                 350

Phe Lys Pro Phe Ala Glu Tyr Lys Ser Asp Tyr Val Tyr Gln Pro Val
    355                 360                 365

Pro Lys Pro Val Trp Glu Gln Leu Phe Gly Trp Leu Thr Lys Pro Gly
370                 375                 380

Ala Gly Ile Met Val Met Asp Pro Tyr Gly Ala Thr Ile Ser Ala Thr
385                 390                 395                 400

Pro Glu Ala Ala Thr Pro Phe Pro His Arg Lys Gly Val Leu Phe Asn
            405                 410                 415

Ile Gln Tyr Val Asn Tyr Trp Phe Ala Glu Ala Gly Ala Ala Pro
        420                 425                 430

Leu Gln Trp Ser Lys Asp Ile Tyr Lys Phe Met Glu Pro Phe Val Ser
    435                 440                 445

Lys Asn Pro Arg Gln Ala Tyr Ala Asn Tyr Arg Asp Ile Asp Leu Gly
450                 455                 460

Arg Asn Glu Val Val Asn Asp Ile Ser Thr Tyr Ser Ser Gly Lys Val
465                 470                 475                 480

Trp Gly Glu Lys Tyr Phe Lys Gly Asn Phe Gln Arg Leu Ala Ile Thr
            485                 490                 495

Lys Gly Lys Val Asp Pro Gln Asp Tyr Phe Arg Asn Gly Gln Ser Ile
        500                 505                 510

Pro Pro Leu Leu Gly Lys
        515

<210> SEQ ID NO 7
<211> LENGTH: 1603
<212> TYPE: DNA
<213> ORGANISM: Triticum aestivum
<220> FEATURE:
<221> NAME/KEY: CDS
<222> LOCATION: (1)..(1557)

<400> SEQUENCE: 7 aac tat agg gcc ttc acg ctg gtg ctc ctc ttc tgc gcc ttg tcc tgt      48
Asn Tyr Arg Ala Phe Thr Leu Val Leu Leu Phe Cys Ala Leu Ser Cys
 1               5                  10                  15 caa gcc gcc gcc acc tac gcg ccg gtg cct gcc aag gag gac ttc ctc      96
Gln Ala Ala Ala Thr Tyr Ala Pro Val Pro Ala Lys Glu Asp Phe Leu
             20                  25                  30 gga tgc ctc atg aag gag ata ccg gca cgc ctc ctc tac gcc aag agc     144
Gly Cys Leu Met Lys Glu Ile Pro Ala Arg Leu Leu Tyr Ala Lys Ser
         35                  40                  45 tcg cct gac ttc ccc acc gtc ctg gcg cag acc atc agg aac tcg cgg     192
Ser Pro Asp Phe Pro Thr Val Leu Ala Gln Thr Ile Arg Asn Ser Arg
     50                  55                  60 tgg ttg tcg ccg cag aac gtg aag ccg ctc tac atc atc acc ccc acc     240
Trp Leu Ser Pro Gln Asn Val Lys Pro Leu Tyr Ile Ile Thr Pro Thr
 65                  70                  75                  80 aac gcc tcg cac atc cag tcc gcg gtg gtg tgc gga cgc cgg cac agc     288
Asn Ala Ser His Ile Gln Ser Ala Val Val Cys Gly Arg Arg His Ser
                 85                  90                  95 gtc cgc ctc cgc gtc cgg agc ggc ggc cac gac tac gag ggc ctg tcg     336
Val Arg Leu Arg Val Arg Ser Gly Gly His Asp Tyr Glu Gly Leu Ser
```

-continued

| | 100 | | | | 105 | | | | | 110 | | | | |
|---|---|---|---|---|---|---|---|---|---|---|---|---|---|---|

```
tac cgg tcc gag aaa ccc gag acg ttc gcc gtc gtc gac ctc aac aag      384
Tyr Arg Ser Glu Lys Pro Glu Thr Phe Ala Val Val Asp Leu Asn Lys
        115                 120                 125 atg cgg gca gtg ttg atc gac ggc tac gcc cgc acg gcg tgg gtc gaa      432
Met Arg Ala Val Leu Ile Asp Gly Tyr Ala Arg Thr Ala Trp Val Glu
130                 135                 140 tcc ggc gcg cag ctc ggc gag ctc tac tac gcc atc gcg aaa aac agc      480
Ser Gly Ala Gln Leu Gly Glu Leu Tyr Tyr Ala Ile Ala Lys Asn Ser
145                 150                 155                 160 ccc gtg ctc gcg ttc ccg gcc ggc gtc tgc ccg acc atc ggc gtc ggc      528
Pro Val Leu Ala Phe Pro Ala Gly Val Cys Pro Thr Ile Gly Val Gly
                165                 170                 175 ggc aac ttc gca ggc ggc ggc ttt ggc atg ctg ctg cgg aag tac ggc      576
Gly Asn Phe Ala Gly Gly Gly Phe Gly Met Leu Leu Arg Lys Tyr Gly
            180                 185                 190 atc gcc gcc gag aac gtc atc gac gtc aag gtg gtc gac ccc aac ggc      624
Ile Ala Ala Glu Asn Val Ile Asp Val Lys Val Val Asp Pro Asn Gly
        195                 200                 205 aag ctt ctc gac aag agc tcc atg agc ccg gac cac ttc tgg gcc gtc      672
Lys Leu Leu Asp Lys Ser Ser Met Ser Pro Asp His Phe Trp Ala Val
210                 215                 220 agg ggc ggc ggc gga gag agc ttt ggc atc gtc gtg tcg tgg caa gtg      720
Arg Gly Gly Gly Gly Glu Ser Phe Gly Ile Val Val Ser Trp Gln Val
225                 230                 235                 240 aag ctc ctg ccg gtg cct ccc acc gtg acc gtg ttc aag atc ccc aag      768
Lys Leu Leu Pro Val Pro Pro Thr Val Thr Val Phe Lys Ile Pro Lys
                245                 250                 255 aca gtg caa gaa ggc gcc gta gac ctc gtc aac aag tgg caa ctg gtc      816
Thr Val Gln Glu Gly Ala Val Asp Leu Val Asn Lys Trp Gln Leu Val
            260                 265                 270 ggg ccg gcc ctt ccc ggc gac ctc atg atc cgc gtc atc gct gcg ggg      864
Gly Pro Ala Leu Pro Gly Asp Leu Met Ile Arg Val Ile Ala Ala Gly
        275                 280                 285 aac acc gcg aca ttc gag ggc atg tac ctg ggc acc tgc caa acc ctg      912
Asn Thr Ala Thr Phe Glu Gly Met Tyr Leu Gly Thr Cys Gln Thr Leu
        290                 295                 300 acg ccg ttg atg agc agc caa ttc ccc gag ctt ggc atg aac ccc tat      960
Thr Pro Leu Met Ser Ser Gln Phe Pro Glu Leu Gly Met Asn Pro Tyr
305                 310                 315                 320 cac tgc aac gag atg ccc tgg atc aag tcc atc ccc ttc atc cac ctc     1008
His Cys Asn Glu Met Pro Trp Ile Lys Ser Ile Pro Phe Ile His Leu
                325                 330                 335 ggc aaa gag gcc agc ctg gtc gac ctc ctc aac cgg aac aac acc ttc     1056
Gly Lys Glu Ala Ser Leu Val Asp Leu Leu Asn Arg Asn Asn Thr Phe
            340                 345                 350 aag ccc ttc gcc gaa tac aag tcg gac tac gtg tac cag ccc ttc ccc     1104
Lys Pro Phe Ala Glu Tyr Lys Ser Asp Tyr Val Tyr Gln Pro Phe Pro
        355                 360                 365 aag ccc gtg tgg gag cag atc ttc ggc tgg ctc acg aag ccc ggt ggg     1152
Lys Pro Val Trp Glu Gln Ile Phe Gly Trp Leu Thr Lys Pro Gly Gly
370                 375                 380 ggg atg atg atc atg gac cca tac ggc gcc acc atc agc gcc acc ccc     1200
Gly Met Met Ile Met Asp Pro Tyr Gly Ala Thr Ile Ser Ala Thr Pro
385                 390                 395                 400 gaa gcg gcg acg ccg ttc cct cac cgc cag ggc gtt ctc ttc aac atc     1248
Glu Ala Ala Thr Pro Phe Pro His Arg Gln Gly Val Leu Phe Asn Ile
                405                 410                 415 cag tac gtc aac tac tgg ttc gcc gag gca gcc gcc gcc gcg ccg ctg     1296
```

```
Gln Tyr Val Asn Tyr Trp Phe Ala Glu Ala Ala Ala Ala Pro Leu
            420                 425                 430 cag tgg agc aag gac atg tac aat ttc atg gag ccg tac gtg agc aag    1344
Gln Trp Ser Lys Asp Met Tyr Asn Phe Met Glu Pro Tyr Val Ser Lys
        435                 440                 445 aac ccc agg cag gcg tac gcc aac tac agg gac att gac ctc ggc agg    1392
Asn Pro Arg Gln Ala Tyr Ala Asn Tyr Arg Asp Ile Asp Leu Gly Arg
450                 455                 460 aac gag gtg gtg aac gac atc tca acc tat agc agc ggc aag gtt tgg    1440
Asn Glu Val Val Asn Asp Ile Ser Thr Tyr Ser Ser Gly Lys Val Trp
465                 470                 475                 480 ggc gag aag tac ttc aag ggc aac ttc caa agg ctc gct att acc aag    1488
Gly Glu Lys Tyr Phe Lys Gly Asn Phe Gln Arg Leu Ala Ile Thr Lys
                485                 490                 495 ggc aag gtg gat cct cag gac tac ttc agg aac gag cag agc atc ccg    1536
Gly Lys Val Asp Pro Gln Asp Tyr Phe Arg Asn Glu Gln Ser Ile Pro
            500                 505                 510 ccg ctg ctc gag aag tac tga tcgaggacct tgcatggaga tttagtgcgt       1587
Pro Leu Leu Glu Lys Tyr
        515 ggttgccgtt tcacat                                                   1603

<210> SEQ ID NO 8
<211> LENGTH: 518
<212> TYPE: PRT
<213> ORGANISM: Triticum aestivum

<400> SEQUENCE: 8

Asn Tyr Arg Ala Phe Thr Leu Val Leu Leu Phe Cys Ala Leu Ser Cys
  1               5                  10                  15

Gln Ala Ala Thr Tyr Ala Pro Val Pro Ala Lys Glu Asp Phe Leu
                 20                  25                  30

Gly Cys Leu Met Lys Glu Ile Pro Ala Arg Leu Leu Tyr Ala Lys Ser
         35                  40                  45

Ser Pro Asp Phe Pro Thr Val Leu Ala Gln Thr Ile Arg Asn Ser Arg
     50                  55                  60

Trp Leu Ser Pro Gln Asn Val Lys Pro Leu Tyr Ile Ile Thr Pro Thr
 65                  70                  75                  80

Asn Ala Ser His Ile Gln Ser Ala Val Val Cys Gly Arg Arg His Ser
                 85                  90                  95

Val Arg Leu Arg Val Arg Ser Gly Gly His Asp Tyr Glu Gly Leu Ser
                100                 105                 110

Tyr Arg Ser Glu Lys Pro Glu Thr Phe Ala Val Val Asp Leu Asn Lys
            115                 120                 125

Met Arg Ala Val Leu Ile Asp Gly Tyr Ala Arg Thr Ala Trp Val Glu
        130                 135                 140

Ser Gly Ala Gln Leu Gly Glu Leu Tyr Tyr Ala Ile Ala Lys Asn Ser
145                 150                 155                 160

Pro Val Leu Ala Phe Pro Ala Gly Val Cys Pro Thr Ile Gly Val Gly
                165                 170                 175

Gly Asn Phe Ala Gly Gly Gly Phe Gly Met Leu Leu Arg Lys Tyr Gly
            180                 185                 190

Ile Ala Ala Glu Asn Val Ile Asp Val Lys Val Val Asp Pro Asn Gly
        195                 200                 205

Lys Leu Leu Asp Lys Ser Ser Met Ser Pro Asp His Phe Trp Ala Val
    210                 215                 220
```

```
Arg Gly Gly Gly Glu Ser Phe Gly Ile Val Ser Trp Gln Val
225                 230                 235                 240

Lys Leu Leu Pro Val Pro Pro Thr Val Thr Val Phe Lys Ile Pro Lys
            245                 250                 255

Thr Val Gln Glu Gly Ala Val Asp Leu Val Asn Lys Trp Gln Leu Val
        260                 265                 270

Gly Pro Ala Leu Pro Gly Asp Leu Met Ile Arg Val Ile Ala Ala Gly
    275                 280                 285

Asn Thr Ala Thr Phe Glu Gly Met Tyr Leu Gly Cys Gln Thr Leu
290                 295                 300

Thr Pro Leu Met Ser Ser Gln Phe Pro Glu Leu Gly Met Asn Pro Tyr
305             310                 315                 320

His Cys Asn Glu Met Pro Trp Ile Lys Ser Ile Pro Phe Ile His Leu
                325                 330                 335

Gly Lys Glu Ala Ser Leu Val Asp Leu Leu Asn Arg Asn Asn Thr Phe
            340                 345                 350

Lys Pro Phe Ala Glu Tyr Lys Ser Asp Tyr Val Tyr Gln Pro Phe Pro
        355                 360                 365

Lys Pro Val Trp Glu Gln Ile Phe Gly Trp Leu Thr Lys Pro Gly Gly
    370                 375                 380

Gly Met Met Ile Met Asp Pro Tyr Gly Ala Thr Ile Ser Ala Thr Pro
385                 390                 395                 400

Glu Ala Ala Thr Pro Phe Pro His Arg Gln Gly Val Leu Phe Asn Ile
                405                 410                 415

Gln Tyr Val Asn Tyr Trp Phe Ala Glu Ala Ala Ala Ala Pro Leu
            420                 425                 430

Gln Trp Ser Lys Asp Met Tyr Asn Phe Met Glu Pro Tyr Val Ser Lys
        435                 440                 445

Asn Pro Arg Gln Ala Tyr Ala Asn Tyr Arg Asp Ile Asp Leu Gly Arg
    450                 455                 460

Asn Glu Val Val Asn Asp Ile Ser Thr Tyr Ser Ser Gly Lys Val Trp
465                 470                 475                 480

Gly Glu Lys Tyr Phe Lys Gly Asn Phe Gln Arg Leu Ala Ile Thr Lys
                485                 490                 495

Gly Lys Val Asp Pro Gln Asp Tyr Phe Arg Asn Glu Gln Ser Ile Pro
            500                 505                 510

Pro Leu Leu Glu Lys Tyr
        515

<210> SEQ ID NO 9
<211> LENGTH: 1603
<212> TYPE: DNA
<213> ORGANISM: Triticum aestivum
<220> FEATURE:
<221> NAME/KEY: CDS
<222> LOCATION: (1)..(1557)

<400> SEQUENCE: 9 aac tgt agg gcc ttc gcg cag gtg ctc ctc ttc ttc gcc ttg tcc tgc      48
Asn Cys Arg Ala Phe Ala Gln Val Leu Leu Phe Phe Ala Leu Ser Cys
  1               5                  10                  15 caa gcc gcc gcc acc tac gcg ccg gtg cct gcc aag gag gac ttc ctc     96
Gln Ala Ala Ala Thr Tyr Ala Pro Val Pro Ala Lys Glu Asp Phe Leu
             20                  25                  30 gga tgc ctc atg aag gag ata ccg gcc cgc ctc ctc tac gcc aag agc    144
Gly Cys Leu Met Lys Glu Ile Pro Ala Arg Leu Leu Tyr Ala Lys Ser
         35                  40                  45
```

```
                                          -continued tcg cct gac tac ccc acc gtg ctg gcg cag acc atc agg aac tcg cgg     192
Ser Pro Asp Tyr Pro Thr Val Leu Ala Gln Thr Ile Arg Asn Ser Arg
     50                  55                  60 tgg tcg acg cag cag aac gtg aag ccg ctg tac atc atc acc ccc acc     240
Trp Ser Thr Gln Gln Asn Val Lys Pro Leu Tyr Ile Ile Thr Pro Thr
65                  70                  75                  80 aac gcc tcc cac atc caa tcc gcg gtg gtg tgc ggc cgg cac ggc         288
Asn Ala Ser His Ile Gln Ser Ala Val Val Cys Gly Arg Arg His Gly
                 85                  90                  95 gtc cgc ctc cgc gtg cgg agc ggc ggc cac gac tac gag ggc ctg tcg    336
Val Arg Leu Arg Val Arg Ser Gly Gly His Asp Tyr Glu Gly Leu Ser
            100                 105                 110 tac cgg tcc gag aaa ccc gag acg ttc gcc gtc gtc gac ctc aac aag    384
Tyr Arg Ser Glu Lys Pro Glu Thr Phe Ala Val Val Asp Leu Asn Lys
        115                 120                 125 atg cgg gca gtg gtt gtc gac ggc tac gcc cgc acg gcg tgg gtc gaa    432
Met Arg Ala Val Val Val Asp Gly Tyr Ala Arg Thr Ala Trp Val Glu
130                 135                 140 tcc ggc gcg cag ctc ggc gag ctc tac tac gcc atc gcg aag aac agc    480
Ser Gly Ala Gln Leu Gly Glu Leu Tyr Tyr Ala Ile Ala Lys Asn Ser
145                 150                 155                 160 ccc gtg ctc gcg ttc ccg gcc ggc gtc tgc ccg tcc atc ggc gtc ggc    528
Pro Val Leu Ala Phe Pro Ala Gly Val Cys Pro Ser Ile Gly Val Gly
                165                 170                 175 ggc aac ttc gca ggc ggc ggc ttc ggc atg ctg ctc gcg aag tac ggc    576
Gly Asn Phe Ala Gly Gly Gly Phe Gly Met Leu Leu Arg Lys Tyr Gly
            180                 185                 190 atc gcc gcc gag aac gtc atc gac gtc aag gtg gtc gac ccc gac ggc    624
Ile Ala Ala Glu Asn Val Ile Asp Val Lys Val Val Asp Pro Asp Gly
        195                 200                 205 aag ctg ctc gac aag agc tcc atg agc gcg gac cac ttc tgg gcc gtc    672
Lys Leu Leu Asp Lys Ser Ser Met Ser Ala Asp His Phe Trp Ala Val
    210                 215                 220 agg ggc ggc ggc gga gag agc ttc ggc atc gtc gtc tcg tgg cag gtg    720
Arg Gly Gly Gly Gly Glu Ser Phe Gly Ile Val Val Ser Trp Gln Val
225                 230                 235                 240 aag ctc atg cca gtg cct ccc acc gtc acc gtg ttt aag atc ccc aag    768
Lys Leu Met Pro Val Pro Pro Thr Val Thr Val Phe Lys Ile Pro Lys
                245                 250                 255 acg gtg caa gaa ggc gcc gta gac ctc gtc aac aag tgg cag ctg gtc    816
Thr Val Gln Glu Gly Ala Val Asp Leu Val Asn Lys Trp Gln Leu Val
            260                 265                 270 ggg ccg gca ctt ccc ggc gac ctc atg atc cgc gtc atc gct gcc ggg    864
Gly Pro Ala Leu Pro Gly Asp Leu Met Ile Arg Val Ile Ala Ala Gly
        275                 280                 285 aac acg gcg acg ttc gag gcc ttg tac ctg ggc acc tgc aaa acc ctg    912
Asn Thr Ala Thr Phe Glu Ala Leu Tyr Leu Gly Thr Cys Lys Thr Leu
    290                 295                 300 acg ccg ctg atg agc agc caa ttc ccc gag ctt ggc atg aac ccc tat    960
Thr Pro Leu Met Ser Ser Gln Phe Pro Glu Leu Gly Met Asn Pro Tyr
305                 310                 315                 320 cac tgc aac gag atg ccc tgg atc aag tcc gtc ccc ttc atc cac ctc   1008
His Cys Asn Glu Met Pro Trp Ile Lys Ser Val Pro Phe Ile His Leu
                325                 330                 335 ggc aaa cag gct ggc ctg gac gac ctc ctc aac cgg aac aac acc ttc   1056
Gly Lys Gln Ala Gly Leu Asp Asp Leu Leu Asn Arg Asn Asn Thr Phe
            340                 345                 350 aag ccc ttc gcc gaa tac aag tcg gac tac gtg tac cag ccc ttc ccc   1104
Lys Pro Phe Ala Glu Tyr Lys Ser Asp Tyr Val Tyr Gln Pro Phe Pro
```

```
                        355                 360                 365
aag ccc gtg tgg gag cag atc ttc ggc tgg ctc gcg aag ccc ggc gcg         1152
Lys Pro Val Trp Glu Gln Ile Phe Gly Trp Leu Ala Lys Pro Gly Ala
    370                 375                 380 ggg atc atg atc atg gac ccc tac ggc gcc acc atc agc gcc acc ccc         1200
Gly Ile Met Ile Met Asp Pro Tyr Gly Ala Thr Ile Ser Ala Thr Pro
385                 390                 395                 400 gaa gcg gcg acg ccg ttc cct cac cgc cag ggc gtc ctc ttc aac atc         1248
Glu Ala Ala Thr Pro Phe Pro His Arg Gln Gly Val Leu Phe Asn Ile
                405                 410                 415 cag tat gtc aac tac tgg ttc gcc gag cca gcc ggc gcc gcg ccg ctg         1296
Gln Tyr Val Asn Tyr Trp Phe Ala Glu Pro Ala Gly Ala Ala Pro Leu
            420                 425                 430 cag tgg agc aag gac att tac aat ttc atg gag ccg tac gtg agc aag         1344
Gln Trp Ser Lys Asp Ile Tyr Asn Phe Met Glu Pro Tyr Val Ser Lys
        435                 440                 445 aac ccc agg cag gcg tac gcc aac tac agg gac atc gac ctc ggc agg         1392
Asn Pro Arg Gln Ala Tyr Ala Asn Tyr Arg Asp Ile Asp Leu Gly Arg
    450                 455                 460 aat gag gtg gtg aac gac atc tca acc tac agc agc ggc aag gtg tgg         1440
Asn Glu Val Val Asn Asp Ile Ser Thr Tyr Ser Ser Gly Lys Val Trp
465                 470                 475                 480 ggc gag aag tac ttc aag agc aac ttc caa agg ctc gcc att acc aag         1488
Gly Glu Lys Tyr Phe Lys Ser Asn Phe Gln Arg Leu Ala Ile Thr Lys
                485                 490                 495 ggc aag gta gat cct cag gac tac ttc agg aat gag caa agc atc ccg         1536
Gly Lys Val Asp Pro Gln Asp Tyr Phe Arg Asn Glu Gln Ser Ile Pro
            500                 505                 510 ccg ctg atc gag aag tac tga tcgaggacct tgcatggaga tttagtgcgt           1587
Pro Leu Ile Glu Lys Tyr
        515 ggttggcgtt tcacat                                                      1603

<210> SEQ ID NO 10
<211> LENGTH: 518
<212> TYPE: PRT
<213> ORGANISM: Triticum aestivum

<400> SEQUENCE: 10

Asn Cys Arg Ala Phe Ala Gln Val Leu Leu Phe Phe Ala Leu Ser Cys
1               5                   10                  15

Gln Ala Ala Thr Tyr Ala Pro Val Pro Ala Lys Glu Asp Phe Leu
            20                  25                  30

Gly Cys Leu Met Lys Glu Ile Pro Ala Arg Leu Leu Tyr Ala Lys Ser
        35                  40                  45

Ser Pro Asp Tyr Pro Thr Val Leu Ala Gln Thr Ile Arg Asn Ser Arg
    50                  55                  60

Trp Ser Thr Gln Gln Asn Val Lys Pro Leu Tyr Ile Ile Thr Pro Thr
65                  70                  75                  80

Asn Ala Ser His Ile Gln Ser Ala Val Val Cys Gly Arg Arg His Gly
                85                  90                  95

Val Arg Leu Arg Val Arg Ser Gly Gly His Asp Tyr Glu Gly Leu Ser
            100                 105                 110

Tyr Arg Ser Glu Lys Pro Glu Thr Phe Ala Val Val Asp Leu Asn Lys
        115                 120                 125

Met Arg Ala Val Val Val Asp Gly Tyr Ala Arg Thr Ala Trp Val Glu
    130                 135                 140
```

```
Ser Gly Ala Gln Leu Gly Glu Leu Tyr Tyr Ala Ile Ala Lys Asn Ser
145                 150                 155                 160

Pro Val Leu Ala Phe Pro Ala Gly Val Cys Pro Ser Ile Gly Val Gly
                165                 170                 175

Gly Asn Phe Ala Gly Gly Phe Gly Met Leu Leu Arg Lys Tyr Gly
            180                 185                 190

Ile Ala Ala Glu Asn Val Ile Asp Val Lys Val Val Asp Pro Asp Gly
        195                 200                 205

Lys Leu Leu Asp Lys Ser Ser Met Ser Ala Asp His Phe Trp Ala Val
    210                 215                 220

Arg Gly Gly Gly Glu Ser Phe Gly Ile Val Val Ser Trp Gln Val
225                 230                 235                 240

Lys Leu Met Pro Val Pro Pro Thr Val Thr Val Phe Lys Ile Pro Lys
                245                 250                 255

Thr Val Gln Glu Gly Ala Val Asp Leu Val Asn Lys Trp Gln Leu Val
            260                 265                 270

Gly Pro Ala Leu Pro Gly Asp Leu Met Ile Arg Val Ile Ala Ala Gly
        275                 280                 285

Asn Thr Ala Thr Phe Glu Ala Leu Tyr Leu Gly Thr Cys Lys Thr Leu
    290                 295                 300

Thr Pro Leu Met Ser Ser Gln Phe Pro Glu Leu Gly Met Asn Pro Tyr
305                 310                 315                 320

His Cys Asn Glu Met Pro Trp Ile Lys Ser Val Pro Phe Ile His Leu
                325                 330                 335

Gly Lys Gln Ala Gly Leu Asp Asp Leu Leu Asn Arg Asn Asn Thr Phe
            340                 345                 350

Lys Pro Phe Ala Glu Tyr Lys Ser Asp Tyr Val Tyr Gln Pro Phe Pro
        355                 360                 365

Lys Pro Val Trp Glu Gln Ile Phe Gly Trp Leu Ala Lys Pro Gly Ala
    370                 375                 380

Gly Ile Met Ile Met Asp Pro Tyr Gly Ala Thr Ile Ser Ala Thr Pro
385                 390                 395                 400

Glu Ala Ala Thr Pro Phe Pro His Arg Gln Gly Val Leu Phe Asn Ile
                405                 410                 415

Gln Tyr Val Asn Tyr Trp Phe Ala Glu Pro Ala Gly Ala Ala Pro Leu
            420                 425                 430

Gln Trp Ser Lys Asp Ile Tyr Asn Phe Met Glu Pro Tyr Val Ser Lys
        435                 440                 445

Asn Pro Arg Gln Ala Tyr Ala Asn Tyr Arg Asp Ile Asp Leu Gly Arg
    450                 455                 460

Asn Glu Val Val Asn Asp Ile Ser Thr Tyr Ser Ser Gly Lys Val Trp
465                 470                 475                 480

Gly Glu Lys Tyr Phe Lys Ser Asn Phe Gln Arg Leu Ala Ile Thr Lys
                485                 490                 495

Gly Lys Val Asp Pro Gln Asp Tyr Phe Arg Asn Glu Gln Ser Ile Pro
            500                 505                 510

Pro Leu Ile Glu Lys Tyr
        515

<210> SEQ ID NO 11
<211> LENGTH: 1503
<212> TYPE: DNA
<213> ORGANISM: Phleum pratense
<220> FEATURE:
<221> NAME/KEY: CDS
```

<222> LOCATION: (1)..(1503)

<400> SEQUENCE: 11

```
tac ttc ccg ccg ccg gct gct aaa gaa gac ttc ctg ggt tgc ctg gtt    48
Tyr Phe Pro Pro Pro Ala Ala Lys Glu Asp Phe Leu Gly Cys Leu Val
 1               5                  10                  15 aaa gaa atc ccg ccg cgt ctg ttg tac gcg aaa tcg tcg ccg gcg tat    96
Lys Glu Ile Pro Pro Arg Leu Leu Tyr Ala Lys Ser Ser Pro Ala Tyr
             20                  25                  30 ccc tca gtc ctg ggg cag acc atc cgg aac tcg agg tgg tcg tcg ccg   144
Pro Ser Val Leu Gly Gln Thr Ile Arg Asn Ser Arg Trp Ser Ser Pro
         35                  40                  45 gac aac gtg aag ccg ctc tac atc atc acc ccc acc aac gtc tcc cac   192
Asp Asn Val Lys Pro Leu Tyr Ile Ile Thr Pro Thr Asn Val Ser His
     50                  55                  60 atc cag tcc gcc gtg gtg tgc ggc cgc cgc cac agc gtc cgc atc cgc   240
Ile Gln Ser Ala Val Val Cys Gly Arg Arg His Ser Val Arg Ile Arg
 65                  70                  75                  80 gtg cgc agc ggc ggg cac gac tac gag ggc ctc tcg tac cgg tct ttg   288
Val Arg Ser Gly Gly His Asp Tyr Glu Gly Leu Ser Tyr Arg Ser Leu
                 85                  90                  95 cag ccc gag acg ttc gcc gtc gtc gac ctc aac aag atg cgg gcg gtg   336
Gln Pro Glu Thr Phe Ala Val Val Asp Leu Asn Lys Met Arg Ala Val
            100                 105                 110 tgg gtg gac ggc aag gcc cgc acg gcg tgg gtg gac tcc ggc gcg cag   384
Trp Val Asp Gly Lys Ala Arg Thr Ala Trp Val Asp Ser Gly Ala Gln
        115                 120                 125 ctc ggc gag ctc tac tac gcc atc tat aag gcg agc ccc acg ctg gcg   432
Leu Gly Glu Leu Tyr Tyr Ala Ile Tyr Lys Ala Ser Pro Thr Leu Ala
    130                 135                 140 ttc ccg gcc ggc gtg tgc ccg acg atc gga gtg ggc ggc aac ttc gcg   480
Phe Pro Ala Gly Val Cys Pro Thr Ile Gly Val Gly Gly Asn Phe Ala
145                 150                 155                 160 ggc ggc ggc ttc ggc atg ctg ctg cgc aag tac ggc atc gcc gcg gag   528
Gly Gly Gly Phe Gly Met Leu Leu Arg Lys Tyr Gly Ile Ala Ala Glu
                165                 170                 175 aac gtc atc gac gtg aag ctc gtc gac gcc aac ggc aag ctc cac gac   576
Asn Val Ile Asp Val Lys Leu Val Asp Ala Asn Gly Lys Leu His Asp
            180                 185                 190 aag aag tcc atg ggc gac gac cat ttc tgg gcc gtc agg ggc ggc ggg   624
Lys Lys Ser Met Gly Asp Asp His Phe Trp Ala Val Arg Gly Gly Gly
        195                 200                 205 ggc gag agc ttc ggc atc gtg gtc gcg tgg cag gtg aag ctc ctg ccg   672
Gly Glu Ser Phe Gly Ile Val Val Ala Trp Gln Val Lys Leu Leu Pro
    210                 215                 220 gtg ccg ccc acc gtg aca ata ttc aag atc tcc aag aca gtg agc gag   720
Val Pro Pro Thr Val Thr Ile Phe Lys Ile Ser Lys Thr Val Ser Glu
225                 230                 235                 240 ggc gcc gtg gac atc atc aac aag tgg caa gtg gtc gcg ccg cag ctt   768
Gly Ala Val Asp Ile Ile Asn Lys Trp Gln Val Val Ala Pro Gln Leu
                245                 250                 255 ccc gcc gac ctc atg atc cgc atc atc gcg cag ggg ccc aag gcc acg   816
Pro Ala Asp Leu Met Ile Arg Ile Ile Ala Gln Gly Pro Lys Ala Thr
            260                 265                 270 ttc gag gcc atg tac ctc ggc acc tgc aaa acc ctg acg ccg ttg atg   864
Phe Glu Ala Met Tyr Leu Gly Thr Cys Lys Thr Leu Thr Pro Leu Met
        275                 280                 285 agc agc aag ttc ccg gag ctc ggc atg aac ccc tcc cac tgc aac gag   912
Ser Ser Lys Phe Pro Glu Leu Gly Met Asn Pro Ser His Cys Asn Glu
    290                 295                 300
```

```
atg tca tgg atc cag tcc atc ccc ttc gtc cac ctc ggc cac agg gac      960
Met Ser Trp Ile Gln Ser Ile Pro Phe Val His Leu Gly His Arg Asp
305                 310                 315                 320 gcc ctc gag gac gac ctc ctc aac cgg aac aac tcc ttc aag ccc ttc     1008
Ala Leu Glu Asp Asp Leu Leu Asn Arg Asn Asn Ser Phe Lys Pro Phe
                325                 330                 335 gcc gaa tac aag tcc gac tac gtc tac cag ccc ttc ccc aag acc gtc     1056
Ala Glu Tyr Lys Ser Asp Tyr Val Tyr Gln Pro Phe Pro Lys Thr Val
            340                 345                 350 tgg gag cag atc ctc aac acc tgg ctc gtc aag ccc ggc gcc ggg atc     1104
Trp Glu Gln Ile Leu Asn Thr Trp Leu Val Lys Pro Gly Ala Gly Ile
        355                 360                 365 atg atc ttc gac ccc tac ggc gcc acc atc agc gcc acc ccg gag tcc     1152
Met Ile Phe Asp Pro Tyr Gly Ala Thr Ile Ser Ala Thr Pro Glu Ser
370                 375                 380 gcc acg ccc ttc cct cac cgc aag ggc gtc ctc ttc aac atc cag tac     1200
Ala Thr Pro Phe Pro His Arg Lys Gly Val Leu Phe Asn Ile Gln Tyr
385                 390                 395                 400 gtc aac tac tgg ttc gcc ccg gga gcc gcc gcg ccc ctc tcg tgg         1248
Val Asn Tyr Trp Phe Ala Pro Gly Ala Ala Ala Ala Pro Leu Ser Trp
                405                 410                 415 agc aag gac atc tac aac tac atg gag ccc tac gtg agc aag aac ccc     1296
Ser Lys Asp Ile Tyr Asn Tyr Met Glu Pro Tyr Val Ser Lys Asn Pro
                420                 425                 430 agg cag gcg tac gca aac tac agg gac atc gac ctc ggc agg aac gag     1344
Arg Gln Ala Tyr Ala Asn Tyr Arg Asp Ile Asp Leu Gly Arg Asn Glu
            435                 440                 445 gtg gtc aac gac gtc tcc acc tac gcc agc ggc aag gtc tgg ggc cag     1392
Val Val Asn Asp Val Ser Thr Tyr Ala Ser Gly Lys Val Trp Gly Gln
        450                 455                 460 aaa tac ttc aag ggc aac ttc gag agg ctc gcc att acc aag ggc aag     1440
Lys Tyr Phe Lys Gly Asn Phe Glu Arg Leu Ala Ile Thr Lys Gly Lys
465                 470                 475                 480 gtc gat cct acc gac tac ttc agg aac gag cag agc atc ccg ccg ctc     1488
Val Asp Pro Thr Asp Tyr Phe Arg Asn Glu Gln Ser Ile Pro Pro Leu
                485                 490                 495 atc aaa aag tac tga                                                 1503
Ile Lys Lys Tyr
500

<210> SEQ ID NO 12
<211> LENGTH: 500
<212> TYPE: PRT
<213> ORGANISM: Phleum pratense

<400> SEQUENCE: 12

Tyr Phe Pro Pro Ala Ala Lys Glu Asp Phe Leu Gly Cys Leu Val
 1               5                  10                  15

Lys Glu Ile Pro Pro Arg Leu Leu Tyr Ala Lys Ser Ser Pro Ala Tyr
                20                  25                  30

Pro Ser Val Leu Gly Gln Thr Ile Arg Asn Ser Arg Trp Ser Ser Pro
            35                  40                  45

Asp Asn Val Lys Pro Leu Tyr Ile Ile Thr Pro Thr Asn Val Ser His
        50                  55                  60

Ile Gln Ser Ala Val Val Cys Gly Arg Arg His Ser Val Arg Ile Arg
65                  70                  75                  80

Val Arg Ser Gly Gly His Asp Tyr Glu Gly Leu Ser Tyr Arg Ser Leu
                85                  90                  95
```

```
Gln Pro Glu Thr Phe Ala Val Val Asp Leu Asn Lys Met Arg Ala Val
                100                 105                 110

Trp Val Asp Gly Lys Ala Arg Thr Ala Trp Val Asp Ser Gly Ala Gln
        115                 120                 125

Leu Gly Glu Leu Tyr Tyr Ala Ile Tyr Lys Ala Ser Pro Thr Leu Ala
    130                 135                 140

Phe Pro Ala Gly Val Cys Pro Thr Ile Gly Val Gly Asn Phe Ala
145                 150                 155                 160

Gly Gly Gly Phe Gly Met Leu Leu Arg Lys Tyr Gly Ile Ala Ala Glu
                165                 170                 175

Asn Val Ile Asp Val Lys Leu Val Asp Ala Asn Gly Lys Leu His Asp
            180                 185                 190

Lys Lys Ser Met Gly Asp Asp His Phe Trp Ala Val Arg Gly Gly Gly
        195                 200                 205

Gly Glu Ser Phe Gly Ile Val Val Ala Trp Gln Val Lys Leu Leu Pro
    210                 215                 220

Val Pro Pro Thr Val Thr Ile Phe Lys Ile Ser Lys Thr Val Ser Glu
225                 230                 235                 240

Gly Ala Val Asp Ile Ile Asn Lys Trp Gln Val Val Ala Pro Gln Leu
                245                 250                 255

Pro Ala Asp Leu Met Ile Arg Ile Ile Ala Gln Gly Pro Lys Ala Thr
            260                 265                 270

Phe Glu Ala Met Tyr Leu Gly Thr Cys Lys Thr Leu Thr Pro Leu Met
        275                 280                 285

Ser Ser Lys Phe Pro Glu Leu Gly Met Asn Pro Ser His Cys Asn Glu
    290                 295                 300

Met Ser Trp Ile Gln Ser Ile Pro Phe Val His Leu Gly His Arg Asp
305                 310                 315                 320

Ala Leu Glu Asp Asp Leu Leu Asn Arg Asn Asn Ser Phe Lys Pro Phe
                325                 330                 335

Ala Glu Tyr Lys Ser Asp Tyr Val Tyr Gln Pro Phe Pro Lys Thr Val
            340                 345                 350

Trp Glu Gln Ile Leu Asn Thr Trp Leu Val Lys Pro Gly Ala Gly Ile
        355                 360                 365

Met Ile Phe Asp Pro Tyr Gly Ala Thr Ile Ser Ala Thr Pro Glu Ser
370                 375                 380

Ala Thr Pro Phe Pro His Arg Lys Gly Val Leu Phe Asn Ile Gln Tyr
385                 390                 395                 400

Val Asn Tyr Trp Phe Ala Pro Gly Ala Ala Ala Pro Leu Ser Trp
            405                 410                 415

Ser Lys Asp Ile Tyr Asn Tyr Met Glu Pro Tyr Val Ser Lys Asn Pro
        420                 425                 430

Arg Gln Ala Tyr Ala Asn Tyr Arg Asp Ile Asp Leu Gly Arg Asn Glu
    435                 440                 445

Val Val Asn Asp Val Ser Thr Tyr Ala Ser Gly Lys Val Trp Gly Gln
        450                 455                 460

Lys Tyr Phe Lys Gly Asn Phe Glu Arg Leu Ala Ile Thr Lys Gly Lys
465                 470                 475                 480

Val Asp Pro Thr Asp Tyr Phe Arg Asn Glu Gln Ser Ile Pro Pro Leu
                485                 490                 495

Ile Lys Lys Tyr
            500
```

```
<210> SEQ ID NO 13
<211> LENGTH: 12
<212> TYPE: PRT
<213> ORGANISM: Dactylus glomerata

<400> SEQUENCE: 13

Asp Ile Tyr Asn Tyr Met Glu Pro Tyr Val Ser Lys
 1               5                  10

<210> SEQ ID NO 14
<211> LENGTH: 11
<212> TYPE: PRT
<213> ORGANISM: Dactylus glomerata

<400> SEQUENCE: 14

Val Asp Pro Thr Asp Tyr Phe Gly Asn Glu Gln
 1               5                  10

<210> SEQ ID NO 15
<211> LENGTH: 17
<212> TYPE: PRT
<213> ORGANISM: Dactylus glomerata

<400> SEQUENCE: 15

Ala Arg Thr Ala Trp Val Asp Ser Gly Ala Gln Leu Gly Glu Leu Ser
 1               5                  10                  15

Tyr

<210> SEQ ID NO 16
<211> LENGTH: 15
<212> TYPE: PRT
<213> ORGANISM: Dactylus glomerata

<400> SEQUENCE: 16

Gly Val Leu Phe Asn Ile Gln Tyr Val Asn Tyr Trp Phe Ala Pro
 1               5                  10                  15

<210> SEQ ID NO 17
<211> LENGTH: 11
<212> TYPE: PRT
<213> ORGANISM: Cynodon dactylon

<400> SEQUENCE: 17

Lys Thr Val Lys Pro Leu Tyr Ile Ile Thr Pro
 1               5                  10

<210> SEQ ID NO 18
<211> LENGTH: 22
<212> TYPE: PRT
<213> ORGANISM: Cynodon dactylon

<400> SEQUENCE: 18

Lys Gln Val Glu Arg Asp Phe Leu Thr Ser Leu Thr Lys Asp Ile Pro
 1               5                  10                  15

Gln Leu Tyr Leu Lys Ser
             20

<210> SEQ ID NO 19
<211> LENGTH: 16
<212> TYPE: PRT
<213> ORGANISM: Cynodon dactylon

<400> SEQUENCE: 19

Thr Val Lys Pro Leu Tyr Ile Ile Thr Pro Ile Thr Ala Ala Met Ile
```

-continued

<210> SEQ ID NO 20
<211> LENGTH: 24
<212> TYPE: PRT
<213> ORGANISM: Cynodon dactylon

<400> SEQUENCE: 20

Leu Arg Lys Tyr Gly Thr Ala Ala Asp Asn Val Ile Asp Ala Lys Val
1               5                   10                  15

Val Asp Ala Gln Gly Arg Leu Leu
            20

<210> SEQ ID NO 21
<211> LENGTH: 14
<212> TYPE: PRT
<213> ORGANISM: Cynodon dactylon

<400> SEQUENCE: 21

Lys Trp Gln Thr Val Ala Pro Ala Leu Pro Asp Pro Asn Met
1               5                   10

<210> SEQ ID NO 22
<211> LENGTH: 15
<212> TYPE: PRT
<213> ORGANISM: Cynodon dactylon

<400> SEQUENCE: 22

Val Thr Trp Ile Glu Ser Val Pro Tyr Ile Pro Met Gly Asp Lys
1               5                   10                  15

<210> SEQ ID NO 23
<211> LENGTH: 19
<212> TYPE: PRT
<213> ORGANISM: Cynodon dactylon
<220> FEATURE:
<221> NAME/KEY: MOD_RES
<222> LOCATION: (8)
<223> OTHER INFORMATION: variable amino acid

<400> SEQUENCE: 23

Gly Thr Val Arg Asp Leu Leu Xaa Arg Thr Ser Asn Ile Lys Ala Phe
1               5                   10                  15

Gly Lys Tyr

<210> SEQ ID NO 24
<211> LENGTH: 23
<212> TYPE: PRT
<213> ORGANISM: Cynodon dactylon

<400> SEQUENCE: 24

Thr Ser Asn Ile Lys Ala Phe Gly Lys Tyr Lys Ser Asp Tyr Val Leu
1               5                   10                  15

Glu Pro Ile Pro Lys Lys Ser
            20

<210> SEQ ID NO 25
<211> LENGTH: 13
<212> TYPE: PRT
<213> ORGANISM: Cynodon dactylon

<400> SEQUENCE: 25

Tyr Arg Asp Leu Asp Leu Gly Val Asn Gln Val Val Gly
1               5                   10

<210> SEQ ID NO 26
<211> LENGTH: 15
<212> TYPE: PRT
<213> ORGANISM: Cynodon dactylon

<400> SEQUENCE: 26

Ser Ala Thr Pro Pro Thr His Arg Ser Gly Val Leu Phe Asn Ile
 1               5                  10                  15

<210> SEQ ID NO 27
<211> LENGTH: 36
<212> TYPE: PRT
<213> ORGANISM: Cynodon dactylon

<400> SEQUENCE: 27

Ala Ala Ala Ala Leu Pro Thr Gln Val Thr Arg Asp Ile Tyr Ala Phe
 1               5                  10                  15

Met Thr Pro Tyr Val Ser Lys Asn Pro Arg Gln Ala Tyr Val Asn Tyr
            20                  25                  30

Arg Asp Leu Asp
        35

<210> SEQ ID NO 28
<211> LENGTH: 14
<212> TYPE: PRT
<213> ORGANISM: Lolium perenne

<400> SEQUENCE: 28

Phe Leu Glu Pro Val Leu Gly Leu Ile Phe Pro Ala Gly Val
 1               5                  10

<210> SEQ ID NO 29
<211> LENGTH: 9
<212> TYPE: PRT
<213> ORGANISM: Lolium perenne

<400> SEQUENCE: 29

Gly Leu Ile Glu Phe Pro Ala Gly Val
 1               5

<210> SEQ ID NO 30
<211> LENGTH: 22
<212> TYPE: DNA
<213> ORGANISM: Secale cereale

<400> SEQUENCE: 30
ggctcccggg gcgaaccagt ag                                           22

<210> SEQ ID NO 31
<211> LENGTH: 23
<212> TYPE: DNA
<213> ORGANISM: Secale cereale

<400> SEQUENCE: 31
accaacgcct cccacatcca gtc                                          23

<210> SEQ ID NO 32
<211> LENGTH: 49
<212> TYPE: DNA
<213> ORGANISM: Secale cereale

<400> SEQUENCE: 32
gataagcttc tcgagtgatt agtactttt gatcagcggc gggatgctc                49

<210> SEQ ID NO 33
<211> LENGTH: 23
<212> TYPE: DNA
<213> ORGANISM: Secale cereale

<400> SEQUENCE: 33
gctctcgatc ggctacaatg gcg                                          23

<210> SEQ ID NO 34
<211> LENGTH: 25
<212> TYPE: DNA
<213> ORGANISM: Secale cereale

<400> SEQUENCE: 34
cacgcactac aaatctccat gcaag                                        25

<210> SEQ ID NO 35
<211> LENGTH: 30
<212> TYPE: DNA
<213> ORGANISM: Secale cereale

<400> SEQUENCE: 35
catgcttgat ccttattcta ctagttgggc                                   30

<210> SEQ ID NO 36
<211> LENGTH: 30
<212> TYPE: DNA
<213> ORGANISM: Secale cereale

<400> SEQUENCE: 36
tacgcacgat ccttattcta ctagttgggc                                   30

<210> SEQ ID NO 37
<211> LENGTH: 30
<212> TYPE: DNA
<213> ORGANISM: Hordeum vulgare

<400> SEQUENCE: 37
gccttgtcct gccaccacgc cgccgccacc                                   30

<210> SEQ ID NO 38
<211> LENGTH: 23
<212> TYPE: DNA
<213> ORGANISM: Hordeum vulgare

<400> SEQUENCE: 38
gctctcgatc ggctacaatg gcg                                          23

<210> SEQ ID NO 39
<211> LENGTH: 25
<212> TYPE: DNA
<213> ORGANISM: Hordeum vulgare

<400> SEQUENCE: 39
cacgcactac aaatctccat gcaag                                        25

<210> SEQ ID NO 40
<211> LENGTH: 30
<212> TYPE: DNA
<213> ORGANISM: Hordeum vulgare

<400> SEQUENCE: 40

-continued

```
catgcttgat ccttattcta ctagttgggc                                   30

<210> SEQ ID NO 41
<211> LENGTH: 23
<212> TYPE: DNA
<213> ORGANISM: Triticum aestivum

<400> SEQUENCE: 41
cacgcactaa atctccatgc aag                                          23

<210> SEQ ID NO 42
<211> LENGTH: 30
<212> TYPE: DNA
<213> ORGANISM: Triticum aestivum

<400> SEQUENCE: 42
tacgcacgat ccttattcta ctagttgggc                                   30

<210> SEQ ID NO 43
<211> LENGTH: 23
<212> TYPE: DNA
<213> ORGANISM: Triticum aestivum

<400> SEQUENCE: 43
aagctctatc gcctacaatg gcg                                          23

<210> SEQ ID NO 44
<211> LENGTH: 25
<212> TYPE: DNA
<213> ORGANISM: Triticum aestivum

<400> SEQUENCE: 44
ggtgctcctc ttctgcgcct tgtcc                                        25
```

DNA SEQUENCE, AND RECOMBINANT PREPARATION OF GROUP 4 MAJOR ALLERGENS FROM CEREALS

This application is a divisional of U.S. patent application Ser. No. 10/583,089, filed on Jun. 15, 2006, which issued as U.S. Pat. No. 7,935,347 on May 3, 2011, which is a US National Phase under §371 of PCT/EP04/13664, filed on Dec. 1, 2004, the disclosures in which are incorporated by reference herein in their entirety.

BACKGROUND OF THE INVENTION

The present invention relates to the provision of DNA sequences of group 4 major allergens from cereals (Triticeae). The invention also encompasses fragments, new combinations of partial sequences and point mutants having a hypoallergenic action. The recombinant DNA molecules and the derived polypeptides, fragments, new combinations of partial sequences and variants can be utilised for the therapy of pollen-allergic diseases. The proteins prepared by recombinant methods can be employed for in vitro and in vivo diagnosis of pollen allergies.

Type 1 allergies are of importance worldwide. Up to 20% of the population in industrialised countries suffer from complaints such as allergic rhinitis, conjunctivitis or bronchial asthma. These allergies are caused by allergens present in the air (aeroallergens) which are released by sources of various origin, such as plant pollen, mites, cats or dogs. Up to 40% of these type 1 allergy sufferers in turn exhibit specific IgE reactivity with grass pollen allergens, inter alia cereal pollen allergens (Freidhoff et al., 1986, J. Allergy Clin. Immunol. 78, 1190-2001). Of the cereal pollen allergens, the allergens of rye have particular importance.

The substances which trigger type 1 allergy are proteins, glycoproteins or polypeptides. After uptake via the mucous membranes, these allergens react with the IgE molecules bonded to the surface of mast cells in sensitised individuals. If two IgE molecules are crosslinked to one another by an allergen, this results in the release of mediators (for example histamine, prostaglandins) and cytokines by the effector cell and thus in the corresponding clinical symptoms.

A distinction is made between major and minor allergens, depending on the relative frequency with which the individual allergen molecules react with the IgE antibodies of allergy sufferers.

The allergens from the pollen of various species from the family of the grasses (Poaceae) are divided into groups which are homologous amongst one another.

In particular, the molecules of major allergen group 4 have high immunological cross-reactivity with one another both with monoclonal murine antibodies and also with human IgE antibodies (Fahlbusch et al., 1993 Clin. Exp. Allergy 23:51-60; Leduc-Brodard et al., 1996, J. Allergy Clin. Immunol. 98:1065-1072; Su et al., 1996, J. Allergy Clin. Immunol. 97:210; Fahlbusch et al., 1998, Clin. Exp. Allergy 28:799-807; Gavrovic-Jankulovic et al., 2000, Invest. Allergol. Clin. Immunol. 10 (6):361-367; Stumvoll et al. 2002, Biol. Chem. 383:1383-1396; Grote et al., 2002, Biol. Chem. 383:1441-1445; Andersson and Lidholm, 2003, Int. Arch. Allergy Immunol. 130:87-107; Mari, 2003, Clin. Exp. Allergy, 33 (1):43-51).

A complete DNA sequence is hitherto not known for any of the group 4 major allergens.

From the group 4 allergen from *Dactylus glomerata*, it has hitherto only been possible for peptides to be obtained by enzymatic degradation and sequenced:

DIYNYMEPYVSK, (SEQ ID NO 13)

VDPTDYFGNEQ, (SEQ ID NO 14)

ARTAWVDSGAQLGELSY (SEQ ID NO 15)
and

GVLFNIQYVNYWFAP.
(SEQ ID NO 16, Leduc-Brodard et al., 1996, J. Allergy Clin. Immunol. 98: 1065-1072)

Peptides have also been obtained from the group 4 allergen of sub-tropical Bermuda grass (*Cynodon dactylon*) by proteolysis and sequenced:

KTVKPLYIITP, (SEQ ID NO 17)

KQVERDFLTSLTKDIPQLYLKS, (SEQ ID NO 18)

TVKPLYIITPITAAMI, (SEQ ID NO 19)

LRKYGTAADNVIDAKVVDAQGRLL, (SEQ ID NO 20)

KWQTVAPALPDPNM, (SEQ ID NO 21)

VTWIESVPYIPMGDK, (SEQ ID NO 22)

GTVRDLLXRTSNIKAFGKY, (SEQ ID NO 23)

TSNIKAFGKYKSDYVLEPIPKKS, (SEQ ID NO 24)

YRDLDLGVNQVVG, (SEQ ID NO 25)

SATPPTHRSGVLFNI (SEQ ID NO 26)
and

AAAALPTQVTRDIYAFMTPYVSKNPRQAYVNYRDLD.
(SEQ ID NO 27, Liaw et al., 2001, Biochem. Biophys. Research Communication 280: 738-743)

For *Lolium perenne*, peptide fragments having the following sequences have been described for the basic group 4 allergen: FLEPVLGLIFPAGV (SEQ ID NO 28) and GLIEFPAGV (SEQ ID NO 29, Jaggi et al., 1989, Int. Arch. Allergy Appl. Immunol. 89: 342-348).

As the first sequence of a group 4 allergen, the still unpublished sequence of Phl p 4 from *Phleum pratense* (SEQ ID NO 11) has been elucidated by the inventors of the present patent application and described in International Application WO 04/000881.

Nothing is hitherto known on the sequences of the group 4 major allergens from cereals (Triceae).

The object on which the present invention was based therefore consisted in the provision of DNA sequences of group 4 major allergens from cereals, in particular the allergen Sec c 4 from rye (*Secale cerale*) (SEQ ID NO 1, 3), Hor v 4 from barley (*Hordeum vulgare*) (SEQ ID NO 5) and Tri a 4 from wheat (*Triticum aestivum*) (SEQ ID NO 7, 9) and of corresponding recombinant DNA molecules on the basis of which the allergens can be expressed as protein and made available, as such or in modified form, for pharmacologically significant exploitation. The sequence of Phl p 4 (SEQ ID NO 11) was the starting point for the present invention.

LIST OF SEQUENCES ACCORDING TO THE INVENTION

The DNA and protein sequences of the mature allergens in accordance with SEQ ID NO 1-10 are preceded by a signal sequence. The encoding region ends with the TGA or TAG stop codons in the DNA sequences.

DNA sequence of Sec c 4. (a) Isoform Sec c 4.01 (SEQ ID NO 1), (b) isoform Sec c 4.02 (SEQ ID NO 3).

Protein sequences (SEQ ID NO 2, 4) derived from the DNA sequences in accordance with SEQ ID NO 1 and 3.

DNA sequence of Hor v 4 (SEQ ID NO 5).

Protein sequence (SEQ ID NO 6) derived from the DNA sequence in accordance with SEQ ID NO 5.

DNA sequence of Tri a 4. (a) Isoform Tri a 4.01 (SEQ ID NO 7), (b) isoform Tri a 4.02 (SEQ ID NO 9).

Protein sequences (SEQ ID NO 8, 10) derived from the DNA sequences in accordance with SEQ ID NO 7 and 9.

DNA sequence of Phl p 4 (SEQ ID NO 11), in accordance with SEQ ID NO 5 from WO 04/000881.

Protein sequence of Phl p 4 (SEQ ID NO 12), in accordance with SEQ ID NO 6 from WO 04/000881.

DESCRIPTION OF THE INVENTION

The present invention now provides for the first time DNA sequences of the cereal pollen major allergens Sec c 4, Hor v 4 and Tri a 4, in accordance with SEQ ID NO 1, 3, 5, 7, and 9.

The present invention therefore relates to DNA molecules selected from the nucleotide sequences in accordance with SEQ ID NO 1, 3, 5, 7, and 9.

The invention furthermore relates to sequences homologous to the DNA sequences according to the invention and corresponding DNA molecules of group 4 allergens from other Poaceae, such as, for example, *Lolium perenne, Dactylis glomerate, Poa pratensis, Cynodon dactylon* and *Holcus lanatus*, which, owing to the sequence homology that exists, hybridise with the DNA sequences according to the invention under stringent conditions, or have immunological cross-reactivity with respect to the allergens according to the invention.

The invention also encompasses fragments, new combinations of partial sequences and point mutants having a hypoallergenic action.

The invention therefore furthermore relates to corresponding partial sequences, a combination of partial sequences, or replacement, elimination or addition mutants which encode an immunomodulatory, T-cell-reactive fragment of a group 4 allergen from the Poaceae.

With knowledge of the DNA sequence of the naturally occurring allergens, it is now possible to prepare these allergens as recombinant proteins which can be used in the diagnosis and therapy of allergic diseases (Scheiner and Kraft, 1995, Allergy 50: 384-391).

A classical approach to effective therapeutic treatment of allergies is specific immunotherapy or hyposensitisation (Fiebig, 1995, Allergo J. 4 (6): 336-339, Bousquet et al., 1998, J. Allergy Clin. Immunol. 102 (4): 558-562). In this method, the patient is injected subcutaneously with natural allergen extracts in increasing doses. However, there is a risk in this method of allergic reactions or even anaphylactic shock. In order to minimise these risks, innovative preparations in the form of allergoids are employed. These are chemically modified allergen extracts which have significantly reduced IgE reactivity, but identical T-cell reactivity compared with the untreated extract (Fiebig, 1995, Allergo J. 4 (7): 377-382).

Even more substantial therapy optimisation would be possible with allergens prepared by recombinant methods. Defined cocktails of high-purity allergens prepared by recombinant methods, optionally matched to the individual sensitisation patterns of the patients, could replace extracts from natural allergen sources since these, in addition to the various allergens, contain a relatively large number of immunogenic, but non-allergenic secondary proteins.

Realistic perspectives which may result in reliable hyposensitisation with expression products are offered by specifically mutated recombinant allergens in which IgE epitopes are specifically deleted without impairing the T-cell epitopes which are essential for therapy (Schramm et al., 1999, J. Immunol. 162: 2406-2414).

A further possibility for therapeutic influencing of the disturbed TH cell equilibrium in allergy sufferers is immunotherapeutic DNA vaccination, which involves treatment with expressible DNA which encodes the relevant allergens. Initial experimental evidence of allergen-specific influencing of the immune response has been furnished in rodents by injection of allergen-encoding DNA (Hsu et al., 1996, Nature Medicine 2 (5): 540-544).

The present invention therefore also relates to a DNA molecule described above or below as medicament and to a corresponding recombinant expression vector as medicament.

The corresponding proteins prepared by recombinant methods can be employed for therapy and for in vitro and in vivo diagnosis of pollen allergies.

For preparation of the recombinant allergen, the cloned nucleic acid is ligated into an expression vector, and this construct is expressed in a suitable host organism. After biochemical purification, this recombinant allergen is available for detection of IgE antibodies by established methods.

The present invention therefore furthermore relates to a recombinant expression vector comprising a DNA molecule described above or below, functionally linked to an expression control sequence, and a host organism transformed with said DNA molecule or said expression vector.

The invention also relates to the use of at one DNA molecule described above or at least one expression vector described above for the preparation of a medicament for the immunotherapeutic DNA vaccination of patients with allergies in the triggering of which group 4 allergens from the Poaceae, preferably Triticeae, in particular Sec c 4, Hor v 4, Tri a 4, are involved and/or for the prevention of such allergies.

As already stated, the invention can be used as an essential component in a recombinant allergen- or nucleic acid-containing preparation for specific immunotherapy. A number of possibilities arise here. On the one hand, the protein with an unchanged primary structure may be a constituent of the preparation. On the other hand, a hypoallergenic (allergoid) form can be used in accordance with the invention for therapy in order to avoid undesired side effects by specific deletion of IgE epitopes of the molecule as a whole or the production of individual fragments which encode T-cell epitopes. Finally, the nucleic acid per se, if ligated with a eukaryotic expression vector, gives a preparation which, when applied directly, modifies the allergic immune state in the therapeutic sense.

The present invention furthermore relates to the polypeptides encoded by one or more of the DNA molecules described above, preferably in their property as medicament.

These are proteins corresponding to an amino acid sequence in accordance with SEQ ID NO 2, 4, 6, 8 or 10. In particular, these are mature proteins (without signal sequence component), beginning with amino acid 23 (SEQ ID NO 2, 4 and 6) and with amino acid 22 (SEQ ID NO 8, 10). The invention furthermore relates to proteins which contain these amino acid sequences or parts of these sequences.

The invention accordingly also relates to a process for the preparation of such polypeptides by cultivation of a host organism and isolation of the corresponding polypeptide from the culture.

The invention likewise relates to the use of at least one polypeptide described above for the preparation of a medicament for the diagnosis and/or treatment of allergies in the triggering of which group 4 allergens from the Poaceae, preferably Triticeae, in particular Sec c 4, Hor v 4, Tri a 4, are involved and for the prevention of such allergies.

When determining the protein and DNA sequences according to the invention, the following procedure was followed:

Sec c 4 from Rye

1. Starting from the DNA sequence of Phl p 4 (SEQ ID NO 12, WO 04/000881), specific primers (Table 1) derived from the Phl p 4 sequence were generated. Five clones were obtained from rye pollen DNA by PCR with primers #87 and #83. The amplified Sec c 4 gene fragment 1 corresponding to these clones encodes a polypeptide corresponding to amino acids 68-401 of Phl p 4 (SEQ ID NO 12).

2. An EST database search was carried out with the partial Sec c 4 sequence. However, no homologous sequences were found in EST data-bases specialising in rye. Instead, individual, homologous, non-overlapping EST fragments were found in EST databases specialising in barley and wheat. Individual EST fragments extend into the 5'-UTR region and others into the 3'-UTR region (UTR=untranslated region) of the corresponding genes.

3. However, a complete group 4 gene from wheat or barley cannot be constructed from the EST sequences found in the databases since these sequences do not overlap and a homologous group 4 gene is not known. However, it was possible to assign these EST sequences with reference to the Phl p 4 sequence (SEQ ID NO 11) and the Sec c 4 fragment obtained in step 1 and these served as template for the preparation of PCR primers.

4. With the aid of primers #195 and #189 prepared in this way, three clones were obtained by PCR. Primer #195 was derived from a barley EST sequence, primer #189 is a Phl p 4-specific primer and overlaps the Phl p 4 stop codon and the codons of the 10 C-terminal Phl p 4 amino acids. The Sec c 4 gene fragment 2 amplified in this way encodes a polypeptide, beginning within the signal sequence and ending with the position corresponding to position 490 of Phl p 4. This polypeptide covers the N terminal of Sec c 4.

5a. Three further clones were obtained by PCR with primers #195 and #202. Both primers were derived from barley EST sequences. The amplified Sec c 4 gene 3 encodes the corresponding amino acids beginning within the signal sequence and ending at the C terminal of Sec c 4. The complete sequence of mature Sec c 4 is thus present in the sequence determined.

The next two steps 5b and 5c serve to double-check the result obtained in step 5a:

5b. A further clone was obtained by PCR with primers #195 and #203. Primer #195 was derived from a barley EST sequence, primer #203 from a wheat EST sequence. The amplified Sec c 4 gene encodes the corresponding amino acids beginning within the signal sequence and ending at the C terminal of Sec c 4. The complete sequence of mature Sec c 4 is therefore present in the sequence determined.

5c. A further clone was obtained by PCR with primers #195 and #198. Also primer #198 The amplified Sec c 4 gene encodes the corresponding amino acids beginning within the signal sequence and ending at the C terminal of Sec c 4. The complete sequence of mature Sec c 4 is therefore present in the sequence determined.

Two isoforms Sec c 4.01 and 4.02 were found. The mature allergens begin with amino acid 23 of the sequences in accordance with SEQ ID NO 2, 4 and 6.

Hor v 4 from Barley

With the aid of the Sec c 4 sequences obtained as described above, homologous EST fragments were found in EST databases of *Hordeum vulgare*. These fragments overlap, but not to give a complete gene. With reference to the EST sequences found, however, it was possible to generate Hor v 4-specific primers, which were used for amplification of the Hor v 4 gene from genomic DNA.

In total, 15 clones were analysed.

4 clones were obtained by PCR with primers #195 and #198.

4 clones were obtained by PCR with primers #195 and #202.

3 clones were obtained by PCR with primers #194 and #198.

4 clones were obtained by PCR with primers #194 and #202.

The derived protein sequence begins within the signal sequence of Hor v 4 and extends to the C-terminal end of the protein (from amino acid 23 of SEQ ID NO 6).

Tri a 4 from Wheat

With the aid of the Sec c 4 sequences obtained as described above, homologous EST fragments were found in EST databases of *Triticum aestivum*. These fragments overlap, but not to give a complete gene. With reference to the EST sequences found, however, it was possible to generate the Tri a 4-specific primers #199, #203, #204 and #206, which were used for amplification of the Tri a 4 gene from genomic DNA.

In total, 13 clones were analysed.

4 clones were obtained by PCR with primers #204 and #203.

4 clones were obtained by PCR with primers #204 and #199.

3 clones were obtained by PCR with primers #206 and #203.

4 clones were obtained by PCR with primers #206 and #199.

The derived protein sequences begin within the signal sequence of Tri a 4 and extend to the C-terminal end of the protein.

Two variants Tri a 4.01 (from amino acid 22 of SEQ ID NO 8) and Tri a 4.02 (from amino acid 22 of SEQ ID NO 10) were found.

In order to prepare the recombinant allergens according to the invention, the DNA sequences in accordance with SEQ ID NO 1, 3, 5, 7 and 9 were incorporated into expression vectors (for example pProEx, pSE 380). *E. coli*-optimised codons were used for the N-terminal amino acids known from the protein sequencing.

After transformation in *E. coli*, expression and purification of the recombinant allergens according to the invention by various separation techniques, the proteins obtained were subjected to a refolding process.

Both allergens can be employed for highly specific diagnosis of grass pollen allergies. This diagnosis can be carried out in vitro by detection of specific antibodies (IgE, IgG1-4, IgA) and reaction with IgE-loaded effector cells (for example basophiles from blood) or in vivo by skin test reactions and provocation at the reaction organ.

The reaction of the allergens according to the invention with T-lymphocytes from grass pollen allergy sufferes can be detected by allergen-specific stimulation of the T-lymphocytes for proliferation and cytokine synthesis both with T-cells in freshly prepared blood lymphocytes and also on established nSec c 4, nHor v 4 or nTri a 4-reactive T-cell lines and clones.

The triplets encoding the cysteines were modified by site-specific mutagenesis in such a way that they encode other amino acids, preferably serine. Both variants in which individual cysteines have been replaced and those in which various combinations of 2 cysteine residues or all cysteines have been modified were prepared. The expressed proteins of these cysteine point mutants have greatly reduced or zero reactivity with IgE antibodies from allergy sufferers, but react with the T-lymphocytes from these patients.

The present invention therefore furthermore relates to a DNA molecule described above or below in which one, a plurality of or all the cysteine residues of the corresponding polypeptide have been replaced with another amino acid by site-specific mutagenesis.

The immunomodulatory activity of hypoallergenic fragments which correspond to polypeptides having T-cell epitopes and that of the hypoallergenic point mutants (for example cysteine replacements) can be detected by their reaction with T-cells from grass pollen allergy sufferers.

Such hypoallergenic fragments or point mutants of the cysteines can be employed as preparations for hyposensitisation of allergy sufferers since they react with the T-cells with equal effectiveness, but result in reduced IgE-mediated side effects owing to the reduced or entirely absent IgE reactivity.

If the nucleic acids encoding the hypoallergenic allergen variants according to the invention or the unmodified DNA molecules according the invention are ligated with a human expression vector, these constructs can likewise be used as preparations for immunotherapy (DNA vaccination).

Finally, the present invention relates to pharmaceutical compositions comprising at least one DNA molecule described above or at least one expression vector described above and optionally further active ingredients and/or adjuvants for the immunotherapeutic DNA vaccination of patients with allergies in the triggering of which group 4 allergens from the Poaceae, preferably Triticeae, in particular Sec c 4, Hor v 4, Tri a 4, are involved and/or for the prevention of such allergies.

A further group of pharmaceutical compositions according to the invention comprises at least one polypeptide described above instead of the DNA and is suitable for the diagnosis and/or treatment of said allergies.

Pharmaceutical compositions in the sense of the present invention comprise, as active ingredients, a polypeptide according to the invention or an expression vector and/or respective pharmaceutically usable derivatives thereof, including mixtures thereof in all ratios. The active ingredients according to the invention can be brought into a suitable dosage form here together with at least one solid, liquid and/or semi-liquid excipient or adjuvant and optionally in combination with one or more further active ingredients.

Particularly suitable adjuvants are immunostimulatory DNA or oligonucleotides having CpG motives.

These compositions can be used as therapeutic agents or diagnostic agents in human or veterinary medicine. Suitable excipients are organic or inorganic substances which are suitable for parenteral administration and do not adversely affect the action of the active ingredient according to the invention. Suitable for parenteral use are, in particular, solutions, preferably oil-based or aqueous solutions, furthermore suspensions, emulsions or implants. The active ingredient according to the invention may also be lyophilised and the resultant lyophilisates used, for example, for the preparation of injection preparations. The compositions indicated may be sterilised and/or comprise adjuvants, such as preservatives, stabilisers and/or wetting agents, emulsifiers, salts for modifying the osmotic pressure, buffer substances and/or a plurality of further active ingredients. Furthermore, sustained-release preparations can be obtained by corresponding formulation of the active ingredient according to the invention—for example by adsorption on aluminium hydroxide.

The invention thus also serves for improving in vitro diagnosis as part of allergen component-triggering identification of the patient-specific sensitisation spectrum. The invention likewise serves for the preparation of significantly improved preparations for the specific immunotherapy of grass pollen allergies.

TABLE 1

Primers used

| Primer number | SEQ ID NO | Sequence |
| --- | --- | --- |
| a) Sec c 4 | | |
| #0083 | 30 | GGCTCCCGGGGCGAACCAGTAG |
| #0087 | 31 | ACCAACGCCTCCCACATCCAGTC |
| #0189 | 32 | GATAAGCTTCTCGAGTGATTAGTACTTTTTGATCAGCGGCGGGATGCTC |
| #0195 | 33 | GCTCTCGATCGGCTACAATGGCG |
| #0198 | 34 | CACGCACTACAAATCTCCATGCAAG |
| #0202 | 35 | CATGCTTGATCCTTATTCTACTAGTTGGGC |
| #0203 | 36 | TACGCACGATCCTTATTCTACTAGTTGGGC |
| a) Hor v 4 | | |
| #0194 | 37 | GCCTTGTCCTGCCACCACGCCGCCGCCACC |
| #0195 | 38 | GCTCTCGATCGGCTACAATGGCG |
| #0198 | 39 | CACGCACTACAAATCTCCATGCAAG |
| #0202 | 40 | CATGCTTGATCCTTATTCTACTAGTTGGGC |
| c) Tri a 4 | | |
| #0199 | 41 | CACGCACTAAATCTCCATGCAAG |
| #0203 | 42 | TACGCACGATCCTTATTCTACTAGTTGGGC |
| #0204 | 43 | AAGCTCTATCGCCTACAATGGCG |
| #0206 | 44 | GGTGCTCCTCTTCTGCGCCTTGTCC |

We claim:

1. An isolated DNA molecule comprising a nucleic acid sequence encoding a polypeptide selected from the group consisting of SEQ ID NO: 2, SEQ ID NO: 4, SEQ ID NO: 6, SEQ ID NO: 8 and SEQ ID NO: 10, wherein said nucleic acid sequence has been codon-optimized for expression of the polypeptide in a host cell that is not a cell of *Secale cereale Hordeum vulgare* or *Triticum aestivum.*

2. A recombinant DNA expression vector or a cloning system comprising an isolated DNA molecule selected from the group consisting of SEQ ID NO: 1, SEQ ID NO: 3, SEQ ID NO: 5, SEQ ID NO: 7 and SEQ ID NO: 9, and a heterologous expression control sequence.

3. A culture comprising a host organism transformed with the recombinant DNA expression vector or cloning system of claim 2.

4. A process for the preparation of a polypeptide encoded by the isolated DNA molecule of claim 1, comprising cultivating a host organism transformed with the DNA molecule and isolating the polypeptide from the culture.

5. A method for the hyposensitization and/or immunotherapy of an allergy triggered by an allergen from Poaceae species, comprising administering to a subject in need thereof an effective amount of at least one DNA molecule of claim 1.

6. A medicament comprising at least one isolated DNA molecule of claim 1 and a carrier.

7. A medicament comprising the recombinant DNA expression vector or cloning system of claim 2 and a carrier.

8. A pharmaceutical composition comprising at least one isolated DNA molecule of claim 1 and a pharmaceutically acceptable adjuvant.

9. A method for the hyposensitization and/or immunotherapy of an allergy triggered by an allergen of Poaceae species, comprising administering to a subject in need thereof an effective amount of the pharmaceutical composition of claim 8.

10. A pharmaceutical composition comprising at least one recombinant DNA expression vector of claim 2 and an adjuvant.

11. A method for the hyposensitization and/or immunotherapy of an allergy triggered by an allergen from Poaceae species, comprising administering to a subject in need thereof an effective amount of the pharmaceutical composition of claim 10.

* * * * *